United States Patent
Gu et al.

(10) Patent No.: US 9,732,379 B2
(45) Date of Patent: Aug. 15, 2017

(54) ENCODED NANOPORE SENSOR FOR MULTIPLEX NUCLEIC ACIDS DETECTION

(71) Applicant: The Curators of the University of Missouri, Columbia, MO (US)

(72) Inventors: Li-Qun Gu, Columbia, MO (US); Xinyue Zhang, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 288 days.

(21) Appl. No.: 14/213,140

(22) Filed: Mar. 14, 2014

(65) Prior Publication Data

US 2014/0309129 A1 Oct. 16, 2014

Related U.S. Application Data

(60) Provisional application No. 61/788,589, filed on Mar. 15, 2013.

(51) Int. Cl.
 C12Q 1/68 (2006.01)
 C07H 21/00 (2006.01)
 G01N 33/487 (2006.01)

(52) U.S. Cl.
 CPC ......... *C12Q 1/6825* (2013.01); *C12Q 1/6876* (2013.01); *G01N 33/48721* (2013.01)

(58) Field of Classification Search
 CPC .... C12Q 1/6876; C12Q 1/6869; C07H 21/00; C07H 21/02; C07H 21/04
 See application file for complete search history.

(56) References Cited

U.S. PATENT DOCUMENTS

| | | | |
|---|---|---|---|
| 6,362,002 | B1 | 3/2002 | Denison et al. |
| 6,428,959 | B1 | 8/2002 | Deamer |
| 9,395,353 | B2 | 7/2016 | Gu et al. |
| 2002/0137089 | A1 | 9/2002 | Deamer |
| 2003/0044816 | A1 | 3/2003 | Denison et al. |
| 2005/0019784 | A1 | 1/2005 | Su et al. |
| 2005/0131211 | A1 | 6/2005 | Bayley et al. |
| 2005/0136408 | A1 | 6/2005 | Tom-Moy et al. |
| 2005/0208574 | A1 | 9/2005 | Bayley et al. |
| 2006/0003458 | A1 | 1/2006 | Golovchenko et al. |
| 2006/0183112 | A1 | 8/2006 | Min et al. |
| 2006/0292605 | A1 | 12/2006 | Kim et al. |
| 2007/0190542 | A1 | 8/2007 | Ling et al. |
| 2007/0190543 | A1 | 8/2007 | Livak |
| 2007/0218471 | A1 | 9/2007 | Kim et al. |
| 2008/0182239 | A1 | 7/2008 | Mullinax et al. |
| 2009/0029477 | A1 | 1/2009 | Meller et al. |
| 2009/0136958 | A1 | 5/2009 | Gershow et al. |
| 2009/0181390 | A1 | 7/2009 | Li et al. |
| 2009/0274870 | A1 | 11/2009 | Harnack et al. |
| 2009/0286969 | A1 | 11/2009 | Esau et al. |
| 2010/0035260 | A1 | 2/2010 | Olasagasti et al. |
| 2010/0099198 | A1 | 4/2010 | Zhao et al. |
| 2010/0148126 | A1 | 6/2010 | Guan et al. |
| 2010/0291548 | A1 | 11/2010 | Sharaf et al. |
| 2011/0003703 | A1 | 1/2011 | Ma et al. |
| 2011/0028334 | A1 | 2/2011 | Hayden |
| 2011/0053284 | A1 | 3/2011 | Meller et al. |
| 2011/0193570 | A1 | 8/2011 | Chen et al. |

FOREIGN PATENT DOCUMENTS

| | | | |
|---|---|---|---|
| WO | 01/42782 | A1 | 6/2001 |
| WO | 03/000920 | A2 | 1/2003 |
| WO | 03/067210 | A2 | 8/2003 |
| WO | 2004/070052 | A2 | 8/2004 |
| WO | 2007/041621 | A2 | 4/2007 |
| WO | 2008/097190 | A1 | 8/2008 |
| WO | 2009/007743 | A1 | 1/2009 |
| WO | 2009/020682 | A2 | 2/2009 |
| WO | 2009/092035 | A2 | 7/2009 |
| WO | 2010/004273 | A1 | 1/2010 |
| WO | 2011/028494 | A2 | 3/2011 |
| WO | 2011/103424 | A2 | 8/2011 |
| WO | WO2011/106583 | * | 9/2011 |
| WO | 2011/126869 | A2 | 10/2011 |
| WO | 2012/009578 | A2 | 1/2012 |
| WO | 2012/083249 | A2 | 6/2012 |

(Continued)

OTHER PUBLICATIONS

Livnah et al., "Three-Dimensional Structures of Avidin and the Avidin-Biotin Complex", Proceedings of the National Acadamy for the Sciences, USA, Jun. 1993, pp. 5076-5080, vol. 90.

Aksimentiev et al., "Imaging alpha-Hemolysin with Molecular Dynamics: Ionic Conductance, Osmotic Permeability, and the Electrostatic Potential Map", Biophysical Journal, 2005, pp. 3745-3761, vol. 88.

Astier et al., "Toward Single Molecular DNA Sequencing: Direct Identification of Ribonucleoside and Deoxyribonucleoside 5'-Monophosphates by Using an Engineered Protein Nanopore Equipped with a Molecular Adapter", Journal of the American Chemical Society, 2006, pp. 1705-1710, vol. 128, No. 5.

Bhattacharya et al., Rectification of the Current in alpha-Hemolysin Pore Depends on the Cation Type: The Alkali Series Probed by Molecular Dynamics Simulations and Experiments, The Journal of Physical Chemistry, 2011, pp. 4255-4264, vol. 115.

(Continued)

*Primary Examiner* — Ethan C. Whisenant
(74) *Attorney, Agent, or Firm* — Thompson Coburn LLP; Charles P. Romano

(57) ABSTRACT

The present invention provides a new and improved multiplexed oligonucleotide detection method based on the nanopore technology with one or more probes containing a sequence with complementarity to the target oligonucleotide, a terminal extension at the probe's 3' terminus, 5' terminus, or both termini and a label attached to the terminus. The improved probes and probe sets enable sensitive, selective, and direct multiplex detection, differentiation and quantification of distinct target oligonucleotides such as miRNAs. The inventive detection method may also be employed as a non-invasive and cost-effective diagnostic method based on miRNA levels in the patient's tissue sample.

17 Claims, 8 Drawing Sheets

(56) References Cited

FOREIGN PATENT DOCUMENTS

WO    2013121201 A1    8/2013

OTHER PUBLICATIONS

Bond et al., "Molecular Dynamics Simulations of DNA within a Nanopore: Arginine-Phosphate Tethering and a Binding/Sliding Mechanism for Translocation", Biochemistry, 2011, pp. 3777-3783, vol. 50.
Butler et al., "Single-molcule DNA detection with an engineered MspA protein nanopore", Proceedings of the National Academy of Science, Dec. 30, 2008, pp. 20647-20652, vol. 105, No. 52.
Fan et al., "Detection of MicroRNAs Using Target-Guided Formation of Conducting Polymer Nanowires in Nanogaps", Journal of the American Chemical Society, 2007, pp. 5437-5443, vol. 129, No. 7.
Gao et al., "A simple method of creating a nanopore-terminated probe for single-molecule enantiomer discrimination", Analytical Chemistry, Jan. 1, 2009, pp. 80-86, vol./No. 81(1).
Howorka et al., "Sequence-specific detection of individual DNA strands using engineered nanopores", Nature Biotechnology, Jul. 2001, pp. 636-639, vol. 19.
Kim et al., "Detecting Translocation of Individual Single Stranded DNA Homopolymers Through a Fabricated Nanopore Chip", Frontiers in Bioscience, 2007, pp. 2978-2983, vol. 12.
Luan et al., "Electric and Electrophoretic Inversion of the DNA Charge in Multivalent Electrolytes", The Royal Society of Chemistry/Soft Matter, 2010. pp. 243-246, vol. 6.
Ma et al., "Biological Nanopores for Single-Molecule Biophysics", ChemBioChem, Jan. 4, 2010, pp. 25-34, vol. 11 No. 1.
Mitchell et al., "Chemical Tags Facilitate the Sensing of Individual DNA Strands with Nanopores", Angewandte Chemie, 2008, pp. 5565-5568.
Nakane et al., "A Nanosensor for Transmembrane Capture and Identification of Single Nucleic Acid Molecules" Biophysical Journal, Jul. 1, 2004, pp. 615-621, vol. 87 No. 1.
Neely et al., "A Single-Molecule Method for the Quantitation of MicroRNA Gene Expression", Nature Methods, 2006, pp. 41-46, vol. 3, No. 1.
Purnell et al., "Discrimination of Single Base Substitutions in a DNA Strand Immobilized in a Biological Nanopore", ACS Nano, 2009, pp. 2533-2538, vol. 3, No. 9.
Purnell et al., "Nucleotide Identification and Orientation Discrimination of DNA Homopolymers Immobilized in a Protein Nanopore", Nano Letters, 2008, pp. 3029-3034, vol. 8, No. 9.
Singer et al., "Nanopore Based Sequence Specific Detection of Duplex DNA for Genomic Profiling", Nano Letters, 2010, pp. 738-742, vol. 10.
Singer et al., "Nanopore-based Sensing of Individual Nucleic Acid Complexes", Israel Journal of Chemistry, 2009, pp. 323-331, vol. 49.
Skinner et al., "Distinguishing Single- and Double-Stranded Nucleic Acid Molecules Using Solid-State Nanopores", Nano Letters, 2009, pp. 2953-2960, vol. 9, No. 8.
Soni et al., Progress Toward Ultrafast DNA Sequencing Using Solid-State Nanopores, Clinical Chemistry, Nov. 1, 2007, pp. 1996-2001, vol. 53 No. 11.
Thomson et al., "Preliminary nanopore cheminformatics analysis of aptamer-target binding strength", BMC Bioinformatics, 2007, 13 pages, vol. 8(Suppl 7).
Wang et al., "In 3108-Pos a Novel Molecular Signature for Discriminating DNA Unzipping in a Nanopore", Biophysical Journal, Jan. 23, 2010, pp. 599A-699A, No. 98, No. 3, Retrieved from the Internet: URL: http://www.sciencedirect.com/science/article/pii/S0006349509050681/pdfft?md5=150abaa4a8a7556592b390e3ca90b724&pid=1-s2.0-S0006349509050681-main.pdf [retrieved on Jan. 17, 2014].
Wang, et al., "Nanopore-Based Detection of Circulating microRNAs in Lung Cancer Patients", Nature Nanotechnology, Apr. 1, 2012, pp. 668-674, vol. 6, No. 10.
Wanunu et al., "Rapid Electronic Detection of Probe-Specific MicroRNAs Using Thin Nanopore Sensors", Nature Nanotechnology, 2010, pp. 807-814, vol. 5.
Winters-Hilt, "Nanopore Detector based analysis of single-molecule conformational kinetics and binding interactions", BMC Bioinformatics, 2006, 27 pages, vol. 7(Supple 2).
Borsenberger et al., "Chemically Labeled Nucleotides and Oligonucleotides Encode DNA for Sensing with Nanopores", Journal of the American Chemists Society, 2009, pp. 7530-7531, vol. 31.
Kumar et al., "PEG-Labeled Nucleotides and Nanopore Detection for Single Molecule DNA Sequencing by Synthesis", Scientific Reports, 2012, pp. 684, vol. 2.
Maglia et al., "Enhanced Translocation of Single DNA Molecules Through a-hemolysin Nanopores by Manipulation of Internal Charge", PNAS, Dec. 16, 2008, pp. 19720-19725, vol. 105 No. 50.
An et al., "Modulation of the Current Signatures of DNA Abasic Site Adducts in the α-Hemolysin Ion Channel", Chemical Communications, Jan. 1, 2012, pp. 11410-11412, vol. 48.
Extended European Search Report for EP 14762829.1 dated Oct. 18, 2016.
Keyser et al., "Optical Tweezers for Force Measurements on DNA in Nanopores", Review of Scientific Instruments, Oct. 26, 2006, pp. 105105-1-105105-9, vol. 77, No. 10.
Reiner et al., "Theory for Polymer Analysis Using Nanopore-Based Single-Molecule Mass Spectrometry", Proceedings of the National Academy of Sciences, Jul. 6, 2010, pp. 12080-12085, vol. 107, No. 27.
Zhang et al., "Programming Nanopore Ion Flow for Encoded Multiplex MicroRNA Detection", ACS Nano, Apr. 22, 2014, pp. 3444-3450, vol. 8, No. 4.
Howorka et al., "Kinetics of Duplex Formation for Individual DNA Strands Within a Single Protein Nanopore", Proceedings of the National Academy of Sciences, Nov. 6, 2001, pp. 12996-13001, vol. 98, No. 23.
Sanchez-Quesada et al., "Single DNA Rotaxanes of a Transmembrane Pore Protein", Angewandte Chemie International Edition, 2004, pp. 3063-3067, vol. 43.
Filing Receipt for U.S. Appl. No. 15/209,443 dated Jul. 21, 2016.
Tian et al., "Designing a Polycationic Probe for Simultaneous Enrichment and Detection of MicroRNAs in a Nanopore", ACS Nano, 2013, pp. 3962-3969, vol. 7 No. 5.
Updated Filing Receipt for U.S. Appl. No. 15/183,152 dated Jul. 29, 2016.

\* cited by examiner

SEQUENCE LISTING

<160> NUMBER OF SEQ ID NOS: 14

<210> SEQ ID NO 1
<211> LENGTH: 23
<212> TYPE: RNA
<213> ORGANISM: Homo sapiens

<400> SEQUENCE: 1
uuaaugcuaa ucgugauagg ggu                          23

<210> SEQ ID NO 2
<211> LENGTH: 53
<212> TYPE: DNA
<213> ORGANISM: Artificial
<220> FEATURE:
<223> OTHER INFORMATION: synthetic

<400> SEQUENCE: 2
acccctatca cgattagcat taaccccccc ccccccccc ccccccccc ccc        53

<210> SEQ ID NO 3
<211> LENGTH: 54
<212> TYPE: DNA
<213> ORGANISM: Artificial
<220> FEATURE:
<223> OTHER INFORMATION: synthetic
<220> FEATURE:
<221> NAME/KEY: modified_base
<222> LOCATION: (26)..(26)
<223> OTHER INFORMATION: 5-Octadiynyl dU

<400> SEQUENCE: 3
acccctatca cgattagcat taaccnccccc ccccccccc ccccccccc cccc       54

<210> SEQ ID NO 4
<211> LENGTH: 22
<212> TYPE: RNA
<213> ORGANISM: Homo sapiens

<400> SEQUENCE: 4
uagcuuauca gacugauguu ga                           22

<210> SEQ ID NO 5
<211> LENGTH: 52
<212> TYPE: DNA
<213> ORGANISM: Artificial
<220> FEATURE:
<223> OTHER INFORMATION: synthetic

<400> SEQUENCE: 5
tcaacatcag tctgataagc taccccccc ccccccccc ccccccccc cc         52

<210> SEQ ID NO 6
<211> LENGTH: 53

<212> TYPE: DNA
<213> ORGANISM: Artificial
<220> FEATURE:
<223> OTHER INFORMATION: synthetic
<220> FEATURE:
<221> NAME/KEY: modified_base
<222> LOCATION: (25)..(25)
<223> OTHER INFORMATION: 5-Octadiynyl dU

<400> SEQUENCE: 6
tcaacatcag tctgataagc taccncccc cccccccccc cccccccccc ccc       53

<210> SEQ ID NO 7
<211> LENGTH: 22
<212> TYPE: RNA
<213> ORGANISM: Homo sapiens

<400> SEQUENCE: 7
cugugcgugu gacagcggcu ga                                        22

<210> SEQ ID NO 8
<211> LENGTH: 52
<212> TYPE: DNA
<213> ORGANISM: Artificial
<220> FEATURE:
<223> OTHER INFORMATION: synthetic

<400> SEQUENCE: 8
tcagccgctg tcacacgcac agcccccccc cccccccccc cccccccccc cc        52

<210> SEQ ID NO 9
<211> LENGTH: 53
<212> TYPE: DNA
<213> ORGANISM: Artificial
<220> FEATURE:
<223> OTHER INFORMATION: synthetic
<220> FEATURE:
<221> NAME/KEY: modified_base
<222> LOCATION: (25)..(25)
<223> OTHER INFORMATION: 5-Octadiynyl dU

<400> SEQUENCE: 9
tcagccgctg tcacacgcac agccncccc cccccccccc cccccccccc ccc       53

<210> SEQ ID NO 10
<211> LENGTH: 24
<212> TYPE: RNA
<213> ORGANISM: Homo sapiens

<400> SEQUENCE: 10
uuuggcaaug guagaacuca cacu                                      24

<210> SEQ ID NO 11
<211> LENGTH: 54
<212> TYPE: DNA
<213> ORGANISM: Artificial
<220> FEATURE:
<223> OTHER INFORMATION: synthetic

<400> SEQUENCE: 11
agtgtgagtt ctaccattgc caaacccccc cccccccccc cccccccccc cccc     54

<210> SEQ ID NO 12
<211> LENGTH: 55
<212> TYPE: DNA
<213> ORGANISM: Artificial
<220> FEATURE:

```
<223> OTHER INFORMATION: synthetic
<220> FEATURE:
<221> NAME/KEY: modified_base
<222> LOCATION: (27)..(27)
<223> OTHER INFORMATION: 5-Octadiynyl dU

<400> SEQUENCE: 12
agtgtgagtt ctaccattgc caaaccnccc cccccccccc cccccccccc ccccc        55

<210> SEQ ID NO 13
<211> LENGTH: 7
<212> TYPE: PRT
<213> ORGANISM: Artificial
<220> FEATURE:
<223> OTHER INFORMATION: synthetic

<400> SEQUENCE: 13

His His His His His His Cys
1               5

<210> SEQ ID NO 14
<211> LENGTH: 5
<212> TYPE: PRT
<213> ORGANISM: Artificial
<220> FEATURE:
<223> OTHER INFORMATION: synthetic

<400> SEQUENCE: 14

Gly Tyr Tyr Tyr Cys
1               5
```

ENCODED NANOPORE SENSOR FOR MULTIPLEX NUCLEIC ACIDS DETECTION

CROSS REFERENCE TO RELATED APPLICATIONS

This U.S. non-provisional patent application claims the benefit of U.S. Provisional Patent Application No. 61/788,589, which was filed Mar. 15, 2013 and is incorporated herein by reference in its entirety.

GRANT STATEMENT

This invention was made with government support under Grant No. R01GM079613 awarded by the National Institute for Health. The Government has certain rights in the invention.

INCORPORATION OF SEQUENCE LISTING

A sequence listing is provided herewith as a part of this U.S. non-provisional patent application via the USPTO's EFS system in the file named "13UMC050_SEQ LIST_ST25.txt" which is 2,831 bytes in size (measured in MS-Windows®), was created on Mar. 13, 2014, and is incorporated herein by reference in its entirety.

BACKGROUND

The nanopore is a molecular scale pore structure fabricated in an insulating membrane that separate solutions on both sides. Individual target molecules passing through the pore characteristically block the pore conductance, resulting in a signature for both target identification and quantization. The nanopore technology provides a unique single-molecule platform for a variety of biotechnological applications, and in particular the next generation DNA sequencing[20-23]. In miRNA detection, the nanopore sensor uses a programmable DNA probe to generate a target-specific signature signal, and can quantify subpicomolar levels of miRNAs (such as cancer-associated miRNAs), and can distinguish single-nucleotide differences between miRNA family members. This approach is potentially useful for quantitative miRNA detection, the discovery of disease markers and non-invasive early diagnosis of diseases such as cancer.

Previously disclosed nanopore-based multiplex detection systems include nanopore detection of multiple divalent metal ions, which used a chelator engineered in the pore lumen to generate distinct signatures[24] and the use of a molecular adapter to discriminate structure-similar compounds, including pharmaceuticals[25], enantiomers[26, 27] and nucleotides[28, 29]. Multiple proteins were also detected in the nanopore by attaching a polymer to the recognition groups.[30] Different lengths of free polyethylene glycol (PEG) translocating through the β-barrel of a nanopore can be separated according to the nanopore conductance levels[33]. It has also been reported that DNA labeled with a polypeptide can generate signatures when trapped in the nanopore[31]. For the tagging method, the chemical modification of DNA with a peptide tag not only slows the DNA translocation speed, but can generate signatures to facilitate the sensing of individual DNA strands[31], including single-base mutations[32]. The nanopore also functions as a single-molecule mass spectrometry to analyze different sized poly (ethylene glycol) (PEG) polymers translocating through the pore[33] and recently, nanopores have been shown to discriminate four bases by detecting four different sized PEG tags released from 5'-phosphate-modified nucleotides[34]. By chemical modification with a crown tag, individual DNA abase sites can be detected during electrophoretic translocation through the nanopore[35]. However, the development of high throughput nanopore arrays, in which each pore measures one oligonucleotide, remains one challenge.

One of the challenges to the clinical application of nanopore detection is that specific disease diagnostics usually requires accurate detection of a biomarker panel that consists of multiple miRNAs, rather than a single miRNA species. For example, the combination of three miRNA biomarkers miR-155, miR-182 and miR-197 can increase lung cancer discrimination power to a sensitivity of 81% and specificity of 87%[4]. This requires simultaneous detection of multiple miRNAs.

Therefore, there is a need to provide a new oligonucleotide detection method based on nano-scale pore structure with improved sensitivity, speedy process, and cost efficiency, as well as providing for multiplex detection.

SUMMARY

Probe molecules, sets of probe molecules, nanopores, kits comprising the probe molecules, sets of probe molecules, and nanopores, and associated methods of use described in the following portions of the specification, drawings, and claims provided herewith. The use of the probe molecules, sets of probe molecules for detection of target nucleic acids is also provided herein.

Provided herein are sets of probe molecules comprising at least a first probe molecule and a second probe molecule, wherein at least two probe molecules comprise:
a) a capture domain that comprises a sequence with complementarity to a target nucleic acid; b) a terminal extension that is covalently linked to the 5' end, the 3' end, or both the 5' end and the 3' end of the capture domain; and c) at least one polymer label attached to at least one of the terminal extension(s), wherein the nucleic acid capture domain of the first probe molecule comprises a sequence with complementarity to first target nucleic acid and the nucleic acid capture domain of the second probe molecule comprises a sequence with complementarity to a second target nucleic acid, and wherein the polymer label of the first probe molecule is different from the polymer label of the second probe molecule and provide for independent detection of the first and second target nucleic acids in a nanopore system. In certain embodiments, the polymer labels of the first and second probe molecules provide for distinct signature conductance blocks when hybridized with their respective targets and subjected to an applied voltage in a nanopore system. In certain embodiments of any of the aforementioned probe sets, the polymer label is a hydrophilic homopolymer or a hydrophilic heteropolymer. In certain embodiments of any of the aforementioned probe sets, the polymer label is selected from the group consisting of a polyglycol, a polyamine, a peptide, an oligonucleotide, and an oligosaccharide. In certain embodiments, the polyglycol is selected from the group consisting of polyethylene glycol (PEG), methoxypolyethylene glycol (MPEG), polypropylene glycol (PPG), polybutylene glycols (PBG), and copolymers thereof. In certain embodiments of any of the aforementioned probe sets, the capture domain and terminal extension are independently selected from the group consisting of nucleic acids and peptide nucleic acids. In certain embodiments of any of the aforementioned probe sets, the terminal extension is covalently linked to the 3' terminus of the capture domain. In certain embodiments of any of the aforementioned probe sets, the terminal extension is selected from the group consisting of poly(dC)$_{(27-33)}$, poly(dG)$_{(27-33)}$, poly(dA)$_{(27-33)}$, poly(dT)$_{(27-33)}$, and poly(dN)$_{(27-33)}$, where N is any combination of cytosine, guanosine, adenosine, thymine, an abase, inosine, xanthosine, 7-methylguanosine, dihydrouridine, and 5-methylcytidine. In certain embodiments of any of the aforementioned probe sets, the probe set comprises at least one additional probe molecule that comprises: a) a capture domain that comprises a sequence with complementarity to a target nucleic acid; b) a terminal extension that is covalently linked to the 5' or 3' end of the capture domain; and c) at least one polymer label attached to at least one of the terminal extension(s), wherein the nucleic acid capture domain of the additional probe molecule(s) comprises a sequence with complementarity to a target nucleic acid that is distinct from the first and second target nucleic acids and wherein the polymer label of each additional probe molecule(s) is different from the polymer label of the first probe molecule, second probe molecule, and any other additional probe molecules and provides for independent detection of the first, second target, and additional target nucleic acids in a nanopore system. In certain embodiments of any of the aforementioned probe sets, the probe set comprises 3, 4, 6, or 8 probe molecules, wherein the capture domain of each of the probe molecules comprises a distinct sequence with complementarity to a distinct target nucleic acid, and wherein the polymer label of each of the probe molecule(s) is different from the polymer label of the other probe molecules and provides for the independent detection of each target nucleic acid that has complementarity to each probe in a nanopore system. In certain embodiments of any of the aforementioned probe sets, the target nucleic acids are distinct genomic DNA, mRNA, a pre-mature miRNA, a mature miRNA, artificial miRNA, non-coding DNA, non-coding RNA, nucleic acid biomarker, or synthetic aptamer molecules. In certain embodiments of any of the aforementioned probe sets, the nucleic acid capture domains of the probe molecules are from about 15 nucleotides to about 30 nucleotides long. In certain embodiments of any of the aforementioned probe sets, at least one nucleic acid capture domain of the first probe molecule or the second probe molecule comprises a sequence that is complementary with the entire sequence of its complementary target nucleic acid. In certain embodiments of any of the aforementioned probe sets, the polymer label attached to the terminal extension of the first probe molecule and the polymer label attached to the terminal extension of the second probe molecule differ in their amount of polymerization. In certain embodiments of any of the aforementioned probe sets, the label attached to the terminal extension of the first probe molecule is a polyethylene glycol of a certain length and the label attached to the extension of the second probe molecule is a polyethylene glycol of a different length than the polyethylene glycol attached to the first probe molecule. In certain embodiments of any of the aforementioned probe sets, the probe set can further comprise a probe with a capture domain comprising a sequence with complementarity to an additional distinct target nucleic acid and, optionally, a terminal domain, wherein the probe lacks a polymer label and provides for independent detection of the additional distinct target nucleic acid. In certain embodiments of any of the aforementioned probe sets, the polymer label is attached to a residue of the terminal extension that is located within nine residues of 5' or 3' covalent linkage of the terminal extension to the capture domain. In certain embodiments of any of the aforementioned probe sets, the polymer label is attached to the second to the fifth residue of the terminal extension that is located 5' or 3' from the covalent linkage to the capture domain.

Also provided herein are methods for detecting at least two distinct single stranded target nucleic acids in a sample with a nanopore system, the method comprising: a) contacting the sample with a set of at least two probe molecules and allowing the probe molecules to hybridize with any target nucleic acids present in the sample to form a hybridized sample, wherein the set of probe molecules comprises at least a first probe molecule and a second probe molecule, both of which comprise: (i) a capture domain that comprises a sequence with complementarity to a target nucleic acid; (ii) a terminal extension that is covalently linked to the 5' end 3' end, or both the 5' end and the 3' end of the capture domain; and (ii) at least one polymer label attached to at least one of the terminal extension(s), wherein the nucleic acid capture domain of the first probe molecule hybridizes with a first target nucleic acid and the nucleic acid capture domain of the second probe molecule hybridizes with a second target nucleic acid, and wherein the polymer label of the first probe molecule is different from the polymer label of the second probe molecule; b) applying a voltage to the hybridized sample mixture in a cis compartment of a dual chamber nanopore system sufficient to trap a hybridized probe/target nucleic acid complex in the nanopore and drive translocation of the hybridized probes and target nucleic acids through a nanopore of the system by an unzipping process, and, c) analyzing an electrical current pattern in the nanopore system over time, wherein presence of the distinct single stranded target nucleic acids in the sample is indicated by occurrence of two distinct signature electrical current blocks corresponding to trapping of each distinct hybridized probe and target nucleic acids in the nanopore. In certain embodiments of any of the aforementioned methods, the presence a first target nucleic acid and the presence of a second target nucleic acid in the sample result in distinct signature electrical current blocks that are distinct signature conductance blocks. In certain embodiments of any of the aforementioned methods, the presence of the first target nucleic acid and the presence of the second target nucleic acid are separately detected. In certain embodiments of any of the aforementioned methods, the probe set further comprises one or more additional probe molecules capable of separately detecting the presence of at least one additional target nucleic acid. In certain embodiments, the additional probe is a probe with a capture domain comprising a sequence with complementarity to an additional distinct target nucleic acid and, optionally, a terminal domain, wherein the probe lacks a polymer label. In certain embodiments of any of the aforementioned methods, the target nucleic acids are distinct genomic DNA, mRNA, a pre-mature miRNA, a mature miRNA, artificial miRNA, non-coding DNA, non-coding RNA, nucleic acid biomarker, or synthetic aptamer molecules. In certain embodiments, the nucleic acid capture domains of the probe molecules are from about 15 nucleotides to about 30 nucleotides long. In certain embodiments of any of the aforementioned methods, at least one nucleic acid capture domain of the first probe molecule or the second probe molecule comprises a sequence that is complementary with the entire sequence of its complementary target nucleic acid. In certain embodiments of any of the aforementioned methods, the polymer label is a hydrophilic homopolymer or a hydrophilic heteropolymer. In certain embodiments of any of the aforementioned methods, the polymer label is selected from the group consisting of a polyglycol, a polyamine, a peptide, an oligonucleotide, and an oligosaccharide. In certain embodiments, the polyglycol is selected from the group consisting of polyethylene glycol (PEG), methoxypolyethylene glycol (MPEG), polypropylene glycol (PPG), polybutylene glycols (PBG), and copolymers thereof. In certain embodiments of any of the aforementioned methods, the capture domain and terminal extension are independently selected from the group consisting of nucleic acids and peptide nucleic acids. In certain embodiments of any of the aforementioned methods, the terminal extension is covalently linked to the 3' terminus of the capture domain. In certain embodiments of any of the aforementioned methods, the terminal extension is selected from the group consisting of poly(dC)$_{(27-33)}$, poly(dG)$_{(27-33)}$, poly(dA)$_{(27-33)}$, poly(dT)$_{(27-33)}$, and poly(dN)$_{(27-33)}$, where N is any combination of cytosine, guanosine, adenosine, thymine, an abase, inosine, xanthosine, 7-methylguanosine, dihydrouridine, and 5-methylcytidine. In certain embodiments of any of the aforementioned methods, the polymer label attached to the terminal extension of the first probe molecule and the polymer label attached to the terminal extension of the second probe molecule differ in their amount of polymerization. In certain embodiments of any of the aforementioned methods, the label attached to the terminal extension of the first probe molecule is a polyethylene glycol of a certain length and the label attached to the extension of the second probe molecule is a polyethylene glycol of a different length than the polyethylene glycol attached to the first probe molecule. In certain embodiments of any of the aforementioned methods, the polymer label is attached to a residue of the terminal extension that is located within nine residues of 5' or 3' covalent linkage of the terminal extension to the capture domain. In certain embodiments of any of the aforementioned methods, the polymer label is attached to the second to the fifth residue of the terminal extension that is located 5' or 3' from the covalent linkage to the capture domain.

Also provided herein are probe molecules comprising: (i) a capture domain that comprises a sequence with complementarity to a target nucleic acid; (ii) a terminal extension that is covalently linked to the 5' end, the 3' end, or both the 5' and 3' end of the capture domain, and (ii) at least one polymer label attached to at least one terminal extension, wherein the probe molecule provides for detection of the target nucleic acid in a nanopore system. In certain embodiments, the nucleic acid capture domain: i) can hybridize with the target nucleic acid or ii) can hybridizes with the target nucleic acid and comprises a sequence that is complementary with a sequence of the target nucleic acid; (b) the terminal extension is a poly(dC)$_{(27-33)}$ that is covalently linked to the 3' terminal of the nucleic acid capture domain, and (c) the polymer label is attached to the poly(dC) terminal extension. In certain embodiments of any of the aforementioned probes, the target nucleic acid is a genomic DNA, an mRNA, a pre-mature or mature miRNA, an artificial miRNA, non-coding DNA or RNA, a nucleic acid biomarker, or a synthetic aptamer. In certain embodiments of any of the aforementioned probes, the nucleic acid capture domain is about 15 nucleotides to about 30 nucleotides long. In certain embodiments of any of the aforementioned probes, the nucleic acid capture domain comprises a sequence that is complementary with the entire sequence of the target nucleic acid. In certain embodiments of any of the aforementioned probes, the poly(dC) terminal extension is a poly(dC)$^{(30)}$ terminal extension. In certain embodiments of any of the aforementioned probes, the polymer label attached to the terminal extension is a homopolymer or a heteropolymer. In certain embodiments of any of the aforementioned probes, the polymer label is a hydrophilic homopolymer or a hydrophilic heteropolymer. In certain embodiments of any of the aforementioned probes, the polymer label is selected from the group consisting of a polyglycol, a polyamine, a peptide, an oligonucleotide, and an oligosaccharide. In certain embodiments of any of the aforementioned probes, the polyglycol is selected from the group consisting of polyethylene glycol (PEG), methoxypolyethylene glycol (MPEG), polypropylene glycol (PPG), polybutylene glycols (PBG), and copolymers thereof. In certain embodiments of any of the aforementioned probes, the capture domain and terminal extension are independently selected from the group consisting of nucleic acids and peptide nucleic acids. In certain embodiments of any of the aforementioned probes, the terminal extension is covalently linked to the 3' terminus of the capture domain. In certain embodiments of any of the aforementioned probes, the terminal extension is selected from the group consisting of poly(dC)$_{(27-33)}$, poly(dG)$_{(27-33)}$, poly(dA)$_{(27-33)}$, poly(dT)$_{(27-33)}$, and poly(dN)$_{(27-33)}$, where N is any combination of cytosine, guanosine, adenosine, thymine, an abase, inosine, xanthosine, 7-methylguanosine, dihydrouridine, and 5-methylcytidine. In certain embodiments of any of the aforementioned probes, the polymer label is attached to a residue of the terminal extension that is located within nine residues of 5' or 3' covalent linkage of the terminal extension to the capture domain. In certain embodiments of any of the aforementioned probes, the polymer label is attached to the second to the fifth residue of the terminal extension that is located 5' or 3' from the covalent linkage to the capture domain. Also provided are methods for detecting at least one distinct single stranded target nucleic acids in a sample with a nanopore system, the method comprising: (a) contacting the sample with a set of at least one of any of the aforementioned probe molecules and allowing the probe molecule to hybridize with any target nucleic acid present in the sample to form a hybridized sample, wherein the set of probe molecules comprises at least a first probe molecule and a second probe molecule; (b) applying a voltage to the hybridized sample mixture in a cis compartment of a dual chamber nanopore system sufficient to trap a hybridized probe/target nucleic acid complex in the nanopore and drive translocation of the hybridized probe and target nucleic acid through a nanopore of the system by an unzipping process, and, (c) analyzing an electrical current pattern in the nanopore system over time, wherein presence of the distinct single stranded target nucleic acid in the sample is indicated by occurrence of a distinct signature electrical current block corresponding to translocation of the hybridized probe and target nucleic acid through the nanopore.

DESCRIPTION OF DRAWINGS

The descriptions of the drawings are as follows:

As shown in FIG. 7, the sensing chamber, 1, includes a cis compartment, 2, and a trans compartment, 3, which are divided by a partition, 4. Both compartments are filled with a pre-selected recording solution such as 1 M KCl. The partition, 4, has an opening, 5, in its center region, over which a lipid bilayer is formed, and the nanopore, 6, is plugged through the lipid bilayer. The power, 7, provides a voltage that is loaded through a pair of electrodes in the two compartments; the current detector, such as a pico-Ampere amplifier, 8, is connected to monitor the current changes. Upon the testing, a mixture sample of the target oligonucleotide, 9, and its complementary probe, 10, is loaded into the cis compartment, 2.

DETAILED DESCRIPTION

In view of the foregoing, it will be seen that the several advantages of the invention are achieved and attained.

DEFINITIONS

As used herein, the phrase "signature conductance block" refers to a ratio ($I_b/I$) of the current blockage resulting from trapping a given nucleic acid/probe complex in a nanopore ($I_b$) to the current passing through an empty nanopores (I).

As used herein, the term "complementarity", when used in reference to two nucleic acids that can hybridize to one another, refers to nucleic acids that are either fully or partially complementary. Thus, a probe nucleic acid can exhibit complementarity to a target nucleic acid when the region of complementarity comprises, one, two, three, four, or more base mismatches.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Further Description of the Embodiments

Robust nanopore sensing system that enables sensitive, selective and direct detection, differentiation and quantification of distinct single strand oligonucleotides in a multiplex format are provided herein. Additionally, the inventive sensing technology can also be employed to distinguish distinct miRNAs in multiplex format. Furthermore, the inventive technology has the potential for non-invasive and cost-effective early diagnosis and continuous monitoring of markers in patients' blood samples.

Figure 7:
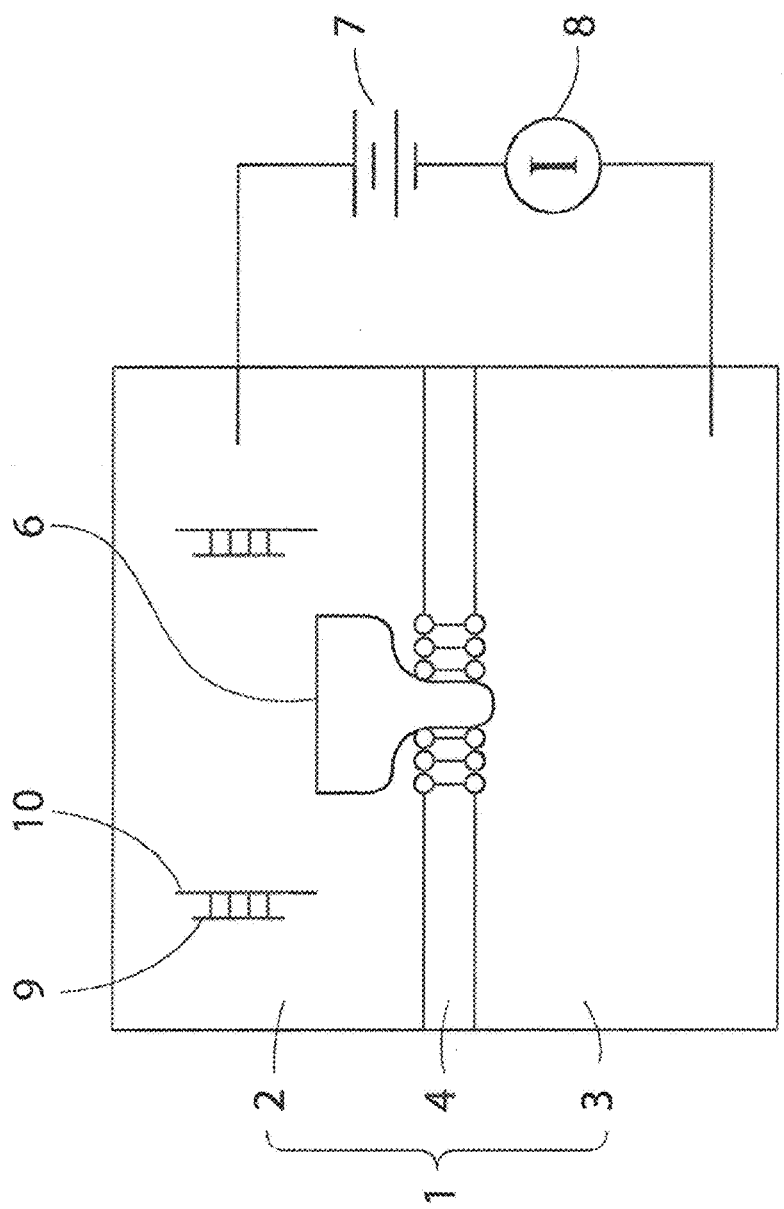
FIG. 7 shows a schematic illustration of an exemplary nanopore sensing system.
Figure 8:
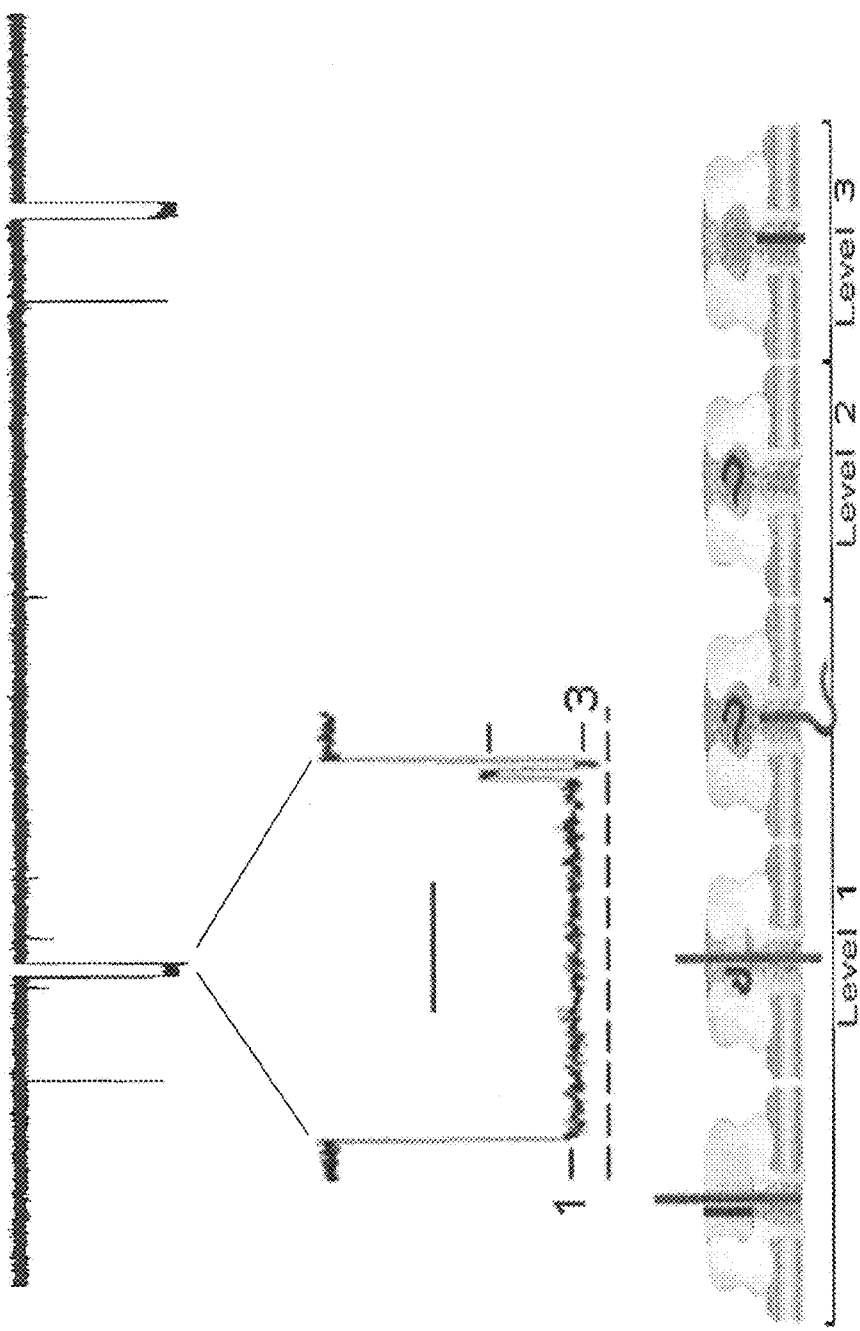
FIG. 8 illustrates an exemplary current trace recorded during an exemplary detection, an amplified electrical mark of a current blockage event, and a schematic illustration of the corresponding unzipping-translocation event associated with the current block.

In one broad aspect, the instant invention is directed to probes, nanopores, kits comprising the probes and nanopores, and associated methods of use, that provide for multiplex analysis of two or more distinct oligonucleotide targets in a sample. In certain embodiments, the probe sets used for multiplex detection provide "signature" current blockage events that distinguish those events arising from interactions with a first probe and a distinct first probe target nucleic acid from other events arising from interactions with a distinct second probe and a second probe target nucleic acid. In certain embodiments, the signature current blockage events used in distinguish events arising from distinct probe molecule/target nucleic acid complexes are "signature conductance blocks" where the ratio ($I_b/I$) of the current blockage resulting from trapping a given nucleic acid/probe complex in a nanopore ($I_b$) to the current passing through an empty nanopores (I) can be distinguished from the ratio ($I_b/I$) resulting from trapping a different nucleic acid/probe complex in a nanopore. Features of such signature current blockage events used to distinguish different probe molecule/target nucleic acid hybridization complexes can also include, but are not limited to, at least one of a: i) current block of different duration; ii) a different number of distinct current blockade levels; iii) a different order of occurrence of current blockade levels than a background current block; or any combination of (i), (ii), or (iii). In certain embodiments, the signature current blockage events used in distinguish events arising from distinct probe molecule/target nucleic acid complexes are at least one of a: i) current block of different duration; ii) a different number of distinct current blockade levels; iii) a different order of occurrence of current blockade levels than a background current block; iv) a signature conductance block; or any combination of (i), (ii), (iii), and/or (iv). In certain embodiments, the signature events are provided in nanopore systems comprising a protein nanopore formed by alpha-hemolysin (αHL) or engineered variants thereof in a planar lipid bilayer system. In certain embodiments, the signature events can be provided in a biochip formed by hydrogel-encapsulated lipid bilayer with a single protein nanopore embedded therein or a micro-droplet bilayer system. Biochips and micro-droplet bilayer systems have been described (Shim and Gu; Stochastic Sensing on a Modular Chip Containing a Single-Ion Channel *Anal. Chem.* 2007, 79, 2207-2213; Bayley, H. et al. Droplet interface bilayers. *Mol. Biosyst.* 4, 1191-1208 (2008). In certain embodiments, the signature events can be provided in a synthetic nanopore. Synthetic nanopores include, but are not limited to, nanopores comprising silicon nitride or graphene. General features of dual compartment nanopore systems are illustrated in FIG. 7. General features of current blockage events resulting from trapping of probe/target nucleic acid hybridization complexes, and subsequent unzipping and translocation of the probe and target are illustrated in FIG. 8. The PCT publication WO2012009578 describes such dual compartment nanopore systems and current blocks resulting from trapping of probe/target nucleic acid hybridization complexes, and subsequent unzipping and translocation of the probe and target. The PCT publication WO2012009578 is incorporated herein by reference in its entirety.

Certain embodiments of the invention provide for one or more a probe molecule(s) for detecting a target nucleic acid. In certain embodiments the target nucleic acid is a single stranded nucleic acid and in certain embodiments the target nucleic acid is a miRNA. The structure of the probe molecule comprises: (i) a nucleic acid capture domain; (ii) one or more terminal extensions covalently linked to the nucleic acid capture domain; and (iii) a label attached to the probe molecule. The nucleic acid capture domain is the portion of the probe that hybridizes to the target nucleic acid to allow for its detection. One of ordinary skill in the art will understand that a target nucleic acid will comprise a nucleic acid sequence. In certain embodiments, the nucleic acid capture domain comprises a sequence that is complementary with a sequence of the target nucleic acid. Target nucleic acids include, but are not limited to, miRNAs that are about 18 to about 24 nucleotides nucleobase residues long. In certain embodiments, the nucleic acid capture domain is from about 15 nucleotides to about 30 nucleotides or nucleobase residues long. In certain embodiments, the nucleic acid capture domain will have at least about 4, 6, 8, 10, 12, 14, 15, 16, 17, 18, 19, 20, 21, 22, 23, 24, or 25 nucleotide or nucleobase residues that are complementary to the target nucleic acid. Generally, the longer the stretch of sequence that is complementary between the capture domain and the target nucleic acid, the more specific the probe will be. In certain embodiments, the nucleic acid capture domain comprises a sequence that is complementary with the entire sequence of the target nucleic acid. The capture domain of probes provided herein is used to capture the target molecule. In certain embodiments, the capture domain can be fully complementary or partially complementary to the target sequence. In certain embodiments, a capture domain can comprise an oligonucleotide comprising natural nucleotides (A, T, G, C (DNA) or a, u, g, c (RNA)), and/or artificial nucleotides including, but not limited to, nucleosides such as inosine, xanthosine, 7-methylguanosine, Dihydrouridine, and 5-methylcytidine. In certain embodiments, the capture domain can comprise a locked nucleic acid (LNA) or a peptide nucleic acid (PNA). Locked nucleic acids comprise RNA derivatives where the ribose ring contains a methylene linkage between the 2-oxygen and the 4-carbon. Peptide nucleic acids (PNA) comprise a peptide backbone with nucleobase side chains. In certain embodiments, a LNA or a PNA capture domain can comprise natural nucleobases (adenine, guanine, thymine, cytosine or uracil) and/or artificial nucleobases including, but not limited to, hypoxanthine, xanthosine, 7-methylguanine, 5,6-dihydrouracil, and 5-methyl cytosine. In certain embodiments, probe capture domains comprising co-polymers of oligonucleotides, LNA, or PNA are provided. In certain embodiments, a capture domain of a probe will have at least about 4, 6, 8, 10, 12, 14, 15, 16, 17, 18, 19, 20, 21, 22, 23, 24, or 25 nucleotide or nucleobase residues that are complementary to the target nucleic acid. In certain embodiments, a central region of a probe will have at least about 4, 6, 8, 10, 12, 14, 15, 16, 17, 18, 19, 20, 21, 22, 23, 24, or 25 to any of about 30, 35, 40, or 50 nucleotide or nucleobase residues that are complementary to the target nucleic acid. In certain embodiments, synthetic nucleotides or nucleobases inserted in the sequence can precisely adjust the hybridization energy with the target, such that one can distinguish the characters of targets such as single-nucleotide polymorphisms, methylation, or interaction between miRNA and its target messenger RNA.

Probe molecules provided herein can comprise terminal extensions at one or both of their 5' and/or 3' termini.

One or more terminal extensions may be covalently linked to the capture domain at the 3' terminal, the 5' terminal, or both. Probe molecule terminal extensions can comprise a charged or hydrophilic polymer of any length. In certain embodiments, the terminal extension polymer can be a negatively charged single-stranded nucleic acid. Advantages of such nucleic acid terminal extensions include, but are not limited to, extremely low cost of synthesis and controllable charge by pH, salt concentration and temperature. Such nucleic acid extensions can comprise homopolymers, heteropolymers, copolymers or combinations thereof. In certain embodiments, the lengths of such nucleic acid terminal extensions can range from about 1 or 2 nucleotides to about 50 nucleotides. In still other embodiments, the nucleic acid extensions can range in length from about 5 to about 40 nucleotides, about 15 to about 35 nucleotides, or from about 20 to about 35 nucleotides. An exemplary terminal extension provided herewith is homopolymer poly(dC)$_{30}$. However, a heteropolymeric sequence, including but not limited to, di- or tri-nucleotide heteropolymers such as CTCTCTCT . . . , or CATCATCAT . . . , can also be used. An abase is a nucleotide without the base, but carries a negative charge provided by the phosphate. As the dimension of abase is narrower than normal nucleotides, it may generate a signature event signal different from that formed by the neighbor nucleotides. In certain embodiments, the terminal extension is a poly(dC) extension. In certain embodiments, the terminal extension is a poly(dC) extension that is covalently linked to the 3' terminal of the capture domain. The length of the poly(dC) extension may be around 30 nucleotides or nucleobase residues, such as between 27 and 33 (poly(dC)(27-33)), and is preferably a poly(dC)(30).

Probe molecule terminal extensions can also comprise a polypeptide. The richer choice of amino acids makes the sequence and functionality of the polypeptide terminal extension more programmable than an oligonucleotide terminal extension. For example, polypeptide terminal extensions allow insertion of charged amino acids in the optimized positions to generate more distinguishable probe/target signature events. While not seeking to be limited by theory, it is believed that the probe/target complex can be selectively trapped using a probe comprising a positively charged polypeptide terminal extension under an appropriate voltage while all other negatively charged non-target oligonucleotides in the mixture are prevented from entering into the pore, resulting in ultra-selective detection. In certain embodiments, the polypeptide terminal extensions can comprise two, three, four, or more amino acid residues that can carry a positive charge (i.e. lysine and/or arginine and/or histidine). In certain embodiments, sufficient numbers of positively charged residues are included in the polypeptide terminal extension to provide a net positive charge when the probe is hybridized to a target oligonucleotide. In certain embodiments where probes comprising terminal extensions with positive charges conferred by residues such as lysine, arginine or histidine, performance of the associated nanopore based detection methods can be enhanced under acidic conditions (i.e. when the pH value is less than 7) or conditions where the residue will be protonated. Thus, the use of such probes at pH values of about 1 to about 6.9, 1 to about 6.0, about 1 to about 5.5, about 3 to about 5.5, and the like. In certain embodiments, the lengths of such polypeptide terminal extensions can range from about 1 or 2 residues to about 30 residues. In still other embodiments, the polypeptide extensions can range in length from about 5 to about 20 residues, about 8 to about 20 residues, or from about 8 to about 15 residues. In an exemplary embodiment, an HIV-TAT polypeptide comprising positively charged arginine and lysine residues can be used as the terminal extension. In certain embodiments, the center domain of the probe that is complementary to the target oligonucleotide can comprise a peptide nucleic acid that is covalently linked to a terminal extension comprising amino acids that carry a positive charge. In certain embodiments, a center domain comprising a peptide nucleic acid is used in conjunction with a terminal extension comprising amino acids that carry a positive charge to provide a net positive charge when the probe is hybridized to a target oligonucleotide. In certain embodiments, polypeptide terminal extensions comprising amino acids with aromatic side chains including, but not limited to, phenylalanine, tryptophan, tyrosine, thyroxine, and the like, can be incorporated into the polypeptide terminal extensions. While not seeking to be limited by theory, it is believed that such aromatic amino acids can interact with the pore through aromatic stacking and provide for useful changes in the signature obtained in nanopore based detection methods.

The label can be attached to the capture domain of the probe molecule, or to a 3' or 5' terminal extension of the probe molecule. In certain embodiments, the label is attached to a 5' or a 3' terminal extension or to both a 5' or a 3' terminal extension. Labels can be also be attached to a 3' terminal extension or a 3' terminal poly(dC) extension. The label may be a polymer, such as a homopolymer or a heteropolymer. In certain embodiments, the label will be at least moderately hydrophilic or hydrophilic. Illustrative examples of polymer labels include oligonucleotides, oligosaccharides, polyamines, polypeptides, and polyglycols. Methods for attaching polyamines to nucleic acids are described in *J. Med. Chem.* 2003, 46, 5478-5483, and methods for attaching peptides to nucleic acids are described in Angew. Chem. Int. Ed. 2008, 47, 5565-5568. The label can be covalently attached to the probe molecule. A label can be attached to a probe molecule via incorporation of a reactive moietie in a residue of a probe molecule. In certain embodiments, a label is attached to the probe molecule via click chemistry. Click chemistry involving metal-catalyzed reactions between azide groups and terminal acetylenes is at least described in U.S. Pat. No. 7,375,234, which is incorporated herein by reference in its entirety. The application of click chemistry to nucleic acids to attach various molecules of interest including peptides and oligosaccharides has also been described (El-Sagheer and Brown *Chem. Soc. Rev.,* 2010, 39, 1388-1405). Methods for derivitizing oligosaccharides for click chemistry applications have been described (Chem. Lett. 2013, 42, 197-199). Various techniques for labeling probe molecules with peptides and crown ethers have also been described[31, 32, 39]. Labels can thus be attached to probes by methods including, but not limited to, $Cu^+$ catalyzed click chemistry, copper free click chemistry which uses cyclo compounds such as cyclooctyne to react with azide, thiol groups reacting with meleimide, Methanethiosulfonate (MTS) attached homo or hetero polymers, and thiol-contained pyridine variations which can be labeled onto nucleotides. One exemplary and non-limiting embodiment of this method is illustrated in Example 4 below. In certain embodiments where a label is covalently attached to a 3' terminal extension, the extension is preferably located within nine residues of the 3' terminus of the capture domain and preferably is located at the second or third residues of the 3' terminus of the capture domain. When hybridized with its target nucleic acid, the hybridized probe molecule can cause a decrease in the signature conductance of a nanopore. When compared to another probe molecule comprising an identical capture domain covalently linked to an identical terminal extension but lacking the label, the labeled probe molecule decreases the signal conductance of the nanopore.

The labels attached to the probe molecules of the probe set may be a polymer molecule, such as but not limited to homopolymers and heteropolymers. Illustrative examples of which include, but are not limited to, oligonucleotides, oligosaccharides, polypeptides, polyamines, and polyglycols. Polyglycol labels that can be used include, but are not limited to, polyethylene glycol (PEG), methoxypolyethylene glycol (MPEG), polypropylene glycol (PPG), polybutylene glycols (PBG), and copolymers thereof. In certain embodiments drawn to a set of probe molecules, the label of one probe molecule differs from the label(s) of other probe molecules in that the labels are different types of polymer molecules. In certain embodiments, the label of one probe molecule differs from the label(s) of other probe molecules in that the labels are the same type of polymer molecule but differ in their amount of polymerization. In certain embodiments, the label attached to the poly(dC) extension of a first probe molecule is a polyethylene glycol of a certain length and the labels attached to the poly(dC) extensions of additional probe molecules are also polyethylene glycol, but of a different length than the polyethylene glycol attached to the first probe molecule and/or of different lengths than labels attached to other probe molecules. Illustrative examples of polyethylene glycol (PEG) of different lengths include, but are not limited to, PEG3, PEGS, and PEG24.

In certain embodiments, a nanopore with a negatively-charged ring at the trans-opening of the pore can be used. In this context, a trans opening of a pore is understood to be that portion of the pore from which a molecule would emerge whereas a cis opening of a pore from which a molecule would enter. In these embodiments, it is understood that a negative charged ring at the trans-opening of the pore can be obtained by using any type of nanopore that has been suitably synthesize and/or derivatized so as to have a negative charged ring at the trans-opening of the pore. Such nanopores with a negatively charged ring at the trans opening of the pore include, but are not limited to, protein nanopores and synthetic nanopores. Protein nanopores with a negatively charged ring at the trans opening of the pore include, but are not limited to, engineered variants of an alpha-hemolysin protein. In certain embodiments, the engineered alpha hemolysin variant can comprise a *Staphylococcus aureus* alpha hemolysin containing a K131D, a K131E, or a K131H amino acid substitution. Exemplary and non-limiting *Staphylococcus aureus* alpha hemolysin wild type sequences are provided in WO2012009578 (as SEQ ID NO:20, nucleic acid coding region; SEQ ID NO:21: protein coding region which are each incorporated herein by reference in their entireties) and which are available elsewhere (National Center for Bioinformatics or GenBank Accession Numbers M90536 and AAA26598). An exemplary and non-limiting *Staphylococcus aureus* alpha hemolysin variant comprising a K131D substitution is provided as SEQ ID NO:22 in WO2012009578. In certain embodiments, the engineered alpha hemolysin variant can comprise a suitably derivatized variant that is derivatized with moieties that provide for a negatively charged ring at the trans opening of the pore. An exemplary wild type *S. aureus* alpha hemolysin protein that can be substituted or derivatized to provide for a protein nanopore with a negative charged ring at the trans-opening of the pore is provided as SEQ ID NO: 21 in WO2012009578. However, variants of other hemolysins capable of forming pores can be substituted or derivatized to provide for a protein nanopore with a negative charged ring at the trans-opening of the pore. Synthetic nanopores with a negatively charged ring at the trans opening of the pore are also provided. In certain embodiments, such synthetic nanopores with a negatively charged ring at the trans opening of the pore include, but are not limited to, silicon nitride or graphene nanopores that have been suitably derivatized with moieties that provide for a negatively charged ring at the trans opening of the pore. The PCT publication WO2012009578 is incorporated herein by reference in its entirety.

Certain embodiments of the invention provide for a set of probe molecules for detecting at least two target nucleic acids, i.e., allowing for multiplexed detection of different target nucleic acids, or allow for comparison between different types of labels when attached to probe molecules that are identical in structure except for the label. The set of probe molecule comprises at least a first probe molecule and a second probe molecule, each comprising the structure of a probe molecule of the invention. In certain embodiments, the nucleic acid capture domain of the first probe molecule hybridizes with a first target nucleic acid and the nucleic acid capture domain of the second probe molecule hybridizes with a second target nucleic acid. In certain embodiments, the label of the first probe molecule is different from the label of the second probe molecule. In certain embodiments, the nucleic acid capture domain of the first probe molecule comprises a sequence that hybridizes with a sequence of a first target nucleic acid and the nucleic acid capture domain of the second probe molecule comprises a sequence that hybridizes with a sequence of a second target nucleic acid, and the label of the first probe molecule is different from the label of the second probe molecule, thus allowing the probe molecule that hybridizes to the first nucleic acid target, and its resultant signal detected in a nanopore detection system, to be distinguished from the probe molecule that hybridizes to the second nucleic acid target, and its resultant signal detected in a nanopore detection system. In certain embodiments, the nucleic acid capture domain of the first probe molecule comprises a sequence that is complementary with a sequence of a first target nucleic acid and the nucleic acid capture domain of the second probe molecule comprises a sequence that is complementary with a sequence of a second target nucleic acid. In certain embodiments, the label of the first probe molecule is different from the label of the second probe molecule. In certain embodiments, the nucleic acid capture domain of the first probe molecule comprises a sequence that is complementary with a sequence of a first target nucleic acid and the nucleic acid capture domain of the second probe molecule comprises a sequence that is complementary with a sequence of a second target nucleic acid, and the label of the first probe molecule is different from the label of the second probe molecule, thus allowing the probe molecule comprising a sequence complementary to the first nucleic acid target, and its resultant signal detected in a nanopore detection system, to be distinguished from the probe molecule comprising a sequence complementary to the second nucleic acid target, and its resultant signal detected in a nanopore detection system.

The probe set may comprise more than two probe molecules, such as for the detection of additional target nucleic acids. Additional probe molecules may comprise a sequence that hybridizes with, or hybridizes with and is complementary with, a target nucleic acid other than the sequence of the first target nucleic acid and/or the sequence of the second target nucleic acid. Additional probe molecules may comprise a label that is different from the label of the first probe molecule and/or the label of the second probe molecule. In certain embodiments, additional probe molecules can also lack a label. In certain embodiments, additional probe molecules may comprise sequences that are hybridize with, or hybridize with and are complementary with the sequence of target nucleic acids, other than the sequences of the first target nucleic acid and the sequence of the second target nucleic acid, and comprise labels different from the label of the first probe molecule and the label of the second probe molecule, thus allowing the additional probe molecules, and their resultant signals detected in a nanopore detection system, to be distinguished from the first, second, and/or other probe molecules in the set of probe molecules.

When hybridized to their target nucleic acids, hybridized probe molecules of this aspect of the invention can in certain embodiments decrease the signature conductance of a nanopore as compared to probe molecules comprising identical capture domains covalently linked to identical terminal extensions but lacking the label, when the probe molecule lacking the label is hybridized to the target nucleic acid. When the label of one probe molecule is different from the label of an additional probe molecule(s)—such as different probe molecules comprising identical capture domains covalently linked to identical terminal extensions, but having different types of labels or labels of different degrees of polymerization—the decrease in signature conductance in a nanopore detection system caused by the hybridized first probe molecule is different from the decrease in signature conductance caused by the hybridized additional probe molecules. This allows for the different probes hybridized to the target nucleic acid and their resultant signals, to be differentially detected in a multiplex nanopore system of the invention. When the label of one probe molecule is different from the label of an additional probe molecule(s)—such as having different types of labels or labels of different degrees of polymerization—and the different probe molecules have different nucleic acid capture domains that hybridize to different target nucleic acids, the decrease in signature conductance caused by the hybridized first probe molecule is different from the decrease in signature conductance caused by the hybridized additional probe molecules, which allows for the different probes hybridized to the different target nucleic acids and their resultant signals, to be differentially detected in a multiplex nanopore system of the invention, thus allowing for the multiplex identification of multiple target nucleic acids.

Certain embodiments of the invention provide for a multiplex method for detecting at least two target nucleic acids. In certain embodiments of the method the target nucleic acids are single stranded nucleic acids and in certain embodiments the single stranded target nucleic acids are miRNA. The target nucleic acids are detected in a sample. Illustrative samples include samples of tissue, blood, or other bodily fluids containing nucleic acids and solutions containing nucleic acids derived therefrom. The sample is contacted with a set of at least a first probe molecule and a second probe molecule comprising structures described herein. The nucleic acid capture domain of the first probe molecule comprises a sequence that recognizes a sequence of a first target nucleic acid and the nucleic acid capture domain of the second probe molecule comprises a sequence that recognizes a sequence of a second target nucleic acid. The label of the first probe molecule is different from the label of the second probe molecule. The probe molecules are allowed to hybridize with nucleic acid targets in the sample to form a hybridized sample of hybridized target nucleic acid•probe complexes. An exemplary hybridization condition is to contact the sample and probe molecules at 95° C. for 10 minutes and then to gradually cool down the mixture to room temperature to form a hybridized sample. The hybridized sample is applied to the cis side of a duel chamber nanopore system and an ionic current is passed through the nanopores of the system. The signature conductance can be measured and the ionic current pattern of the nanopore system is analyzed over time. A decrease in conductance level is indicative of a hybridized probe trapped in a nanopore. Because the presence in the sample of a first target nucleic acid that hybridizes to a first probe molecule with a certain label and the presence of a second target nucleic acid with a different label cause different levels of decreased conductance, the presence and quantity of the first probe molecule and the second probe molecule can be separately detected in a multiplex manner.

A variety of target nucleic acids or oligonucleotides that can be detected and distinguished from other target nucleic acids in multiplexed assays by the probe molecules, probe molecule sets, nanopores, kits comprising the probe molecules and probe molecule sets, and associated use of the probe molecules and probe molecule sets in methods that are provided herein. In certain embodiments, the target can be a nucleic acid or a fragment thereof from cells, body fluid, tissues, bacteria, or a virus. In certain embodiments, the target can be a PCR products or a synthetic oligonucleotide. In certain embodiments, a target can comprise a genomic DNA, an mRNA, a pre-mature or mature miRNA, an artificial miRNA, non-coding DNA or RNA, a nucleic acid biomarker, or a synthetic aptamer. In certain embodiments, a miRNA targets may come from the RNA extraction from bio-fluid from any tissues such as plasma and formalin-fixed and paraffin-embedded tissues. In certain embodiments, a target nucleic acid can comprise a nucleic acid fragment complexed with any of a nucleic acid binding protein, an antibody, or an aptamer bound with a target protein. In certain embodiments, a target nucleic acid can comprise a nucleic acid fragment complexed with a low molecule weight compound, including, but not limited to, a drug. In certain embodiments, targets can include sequences with mutations, with single-nucleotide polymorphisms, or with chemical modifications such as methylation and phosphorylation.

Figure 1:
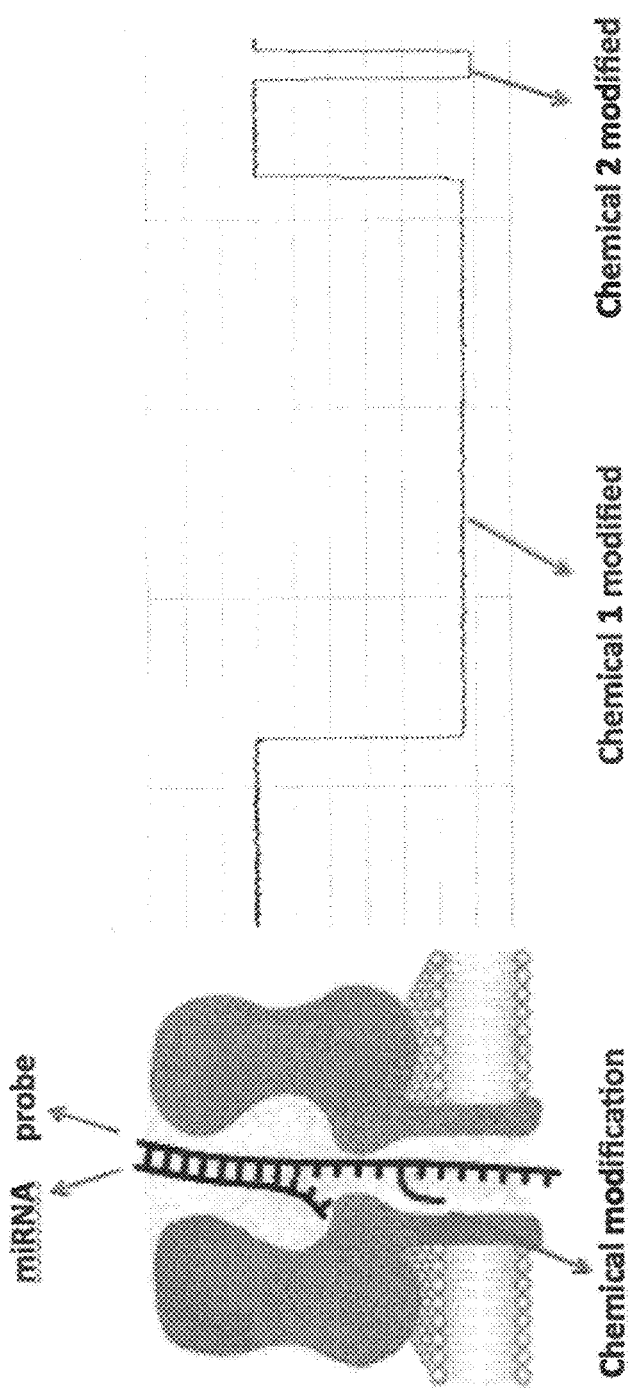
FIG. 1 shows the principle of probe-encoded nanopore multiplex detection of nucleic acids. As shown in the model (Left), the miRNA•probe hybrid is trapped in an α-hemolysin protein nanopore. Each probe is labeled with a characteristic tag (red). Different miRNAs are detected by using differently-tagged probes. These tagged probes trapped in sensing zone of the nanopore (left) can generate signature blocks at distinct conductance levels (right). As a result, multiple miRNAs in the sample can be identified based on their signatures profiles and accurately quantized by counting the occurring frequency of each type of signatures.

Research indicates that aberrant miRNA levels are associated with the development of many cancers, suggesting the potential of miRNAs as cancer biomarkers[2]. miRNAs can also be released from tissues into blood with remarkable stability[3, 4], making the detection of circulating miRNAs a novel strategy for non-invasive cancer diagnosis and prognosis[3-5]. Certain aspects of the invention provide for a nanopore single-molecule sensor for accurate detection of circulating miRNAs without the need for labels or amplification of the miRNA[6]. For example, detection of circulating miRNAs from cancer patients such as lung cancer patients. A barcode strategy utilizes a series of label-encoded probes to simultaneously detect multiple miRNA biomarkers by using one nanopore. This is a novel multiplex miRNA detection method. Each probe is chemically labeled with a barcode label (FIG. 1 left panel). The trapping of the barcode labels in sensing zone of the pore generate distinct signature conductance levels, which allows identification of the type of miRNA hybridized by the probe. As shown by the example in FIG. 1 right panel, the probes labeled with Label (Tag) 1 and Label (Tag) 2 produce two distinct signatures. By separating the conductance levels, the miRNA species bound by the two probes can be discriminated, and multiplex miRNAs can be detected simultaneously in one pore.

The embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

Example 1

Multiplex Nucleic Acid Detection

1. Materials and Methods
Chemicals:
 1. 11-Azido-3,6,9-trioxaundecan-1-amine (PEG3) (Jena Bioscience, Germany)

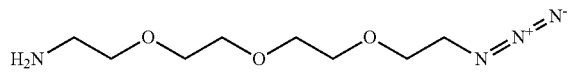

2. O-(2-Aminoehyl)-O'-(2-azideoethyl)heptaethylene glycol (PEGS) (Jena Bioscience, Germany)

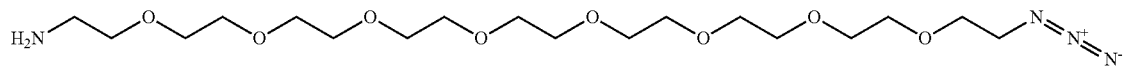 [SMILES: [N-]=[N+]=NCCOCCOCCOCCOCCOCCOCCOCCOCCN]

3. 1-[2-(2-2-[2-(2-2-[2-(2-2-[2-(2-Azido-ethoxy)-ethoxy]-ethoxy-ethoxy)-ethoxy]-ethoxy-ethoxy)-ethoxy]-ethoxy-ethoxy)-ethoxy]-2-methoxy-ethane (PEG24) (Jena Bioscience, Germany)

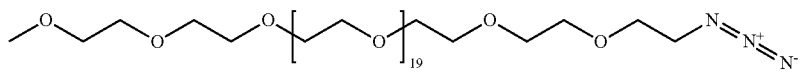

4. Sodium Acetate (CH₃COONa, S8750-500G) (Sigma-Aldrich, St. Louis, Mo.)
5. Copper (I) Bromide (CuBr, 254185-10G) (Sigma-Aldrich, St. Louis, Mo.)
6. Ethanol (CH₃COOH, E7023-500ML) (Sigma-Aldrich, St. Louis, Mo.)
7. Tert-Butanol ((CH₃)₃COH, 471712-100ML) (Sigma-Aldrich, St. Louis, Mo.)
8. Dimethyl Sulfoxide (DMSO, (CH₃)₂SO, D8418-50ML) (Sigma-Aldrich, St. Louis, Mo.)
9. Tris[(1-benzyl-1H-1,2,3-triazol-4yl)methyl]amine (TBTA, 678937-50MG) (Sigma-Aldrich, St. Louis, Mo.)

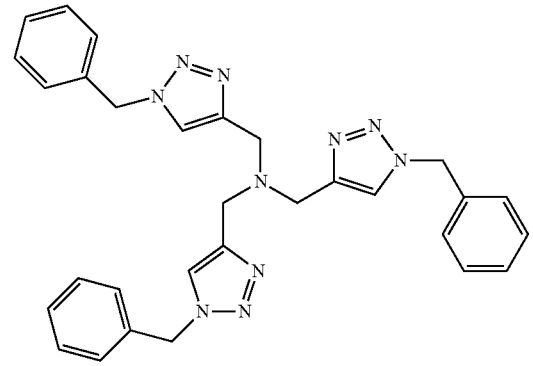 [SMILES: c1ccc(Cn2cc(CN(Cc3cn(Cc4ccccc4)nn3)Cc3cn(Cc4ccccc4)nn3)nn2)cc1]

10. Nuclease Free Water (Integrated DNA Technologies, Coralville, Iowa)

DNAs and RNAs:

All miRNAs and their DNA probes (standard desalting) were synthesized by Integrated DNA Technologies. For each miRNA, one probe flanks a 3' poly(C)₃₀ overhang, the other is inserted with an internal 5-Octadiynyl dU between the 2ⁿᵈ and the 3ʳᵈ cytosines for click chemistry. The RNA and DNA sequences are given below.

```
1. miR-155
                                              (SEQ ID NO: 1)
rUrUrArArUrGrCrUrArArUrCrGrUrGrArUrArGrGrGrU 2. miR-155-probe-C30
                                              (SEQ ID NO: 2)
ACC CCT ATC ACG ATT AGC ATT AAC CCC CCC CCC CCC

CCC CCC CCC CCC CCC CC 3. miR-155-probe-C30-alkyne2
                                              (SEQ ID NO: 3)
ACC CCT ATC ACG ATT AGC ATT AAC CNCC CCC CCC CCC

CCC CCC CCC CCC CCC CC 4. miR-21
                                              (SEQ ID NO: 4)
rUrArGrCrUrUrArUrCrArGrArCrUrGrArUrGrUrUrGrA 5. miR-21-probe-C30
                                              (SEQ ID NO: 5)
T CAA CAT CAG TCT GAT AAG CTA CCC CCC CCC CCC CCC

CCC CCC CCC CCC CCC 6. miR-21-probe-C30-alkyne2
                                              (SEQ ID NO: 6)
T CAA CAT CAG TCT GAT AAG CTA CC/i5OctdU/C CCC CCC

CCC CCC CCC CCC CCC CCC CCC 7. miR-210
                                              (SEQ ID NO: 7)
rCrUrGrUrGrCrGrUrGrUrGrArCrArGrCrGrGrCrUrGrA 8. miR-210-probe-C30
                                              (SEQ ID NO: 8)
TCA GCC GCT GTC ACA CGC ACA GCC CCC CCC CCC CCC

CCC CCC CCC CCC CCC C 9. miR-210-probe-C30-alkyne2
(internal 5-Octadiynyl dU modification)
                                              (SEQ ID NO: 9)
TCA GCC GCT GTC ACA CGC ACA GCC/i5OctdU/CCC CCC

CCC CCC CCC CCC CCC CCC CCC C 10. miR-182-5p
                                              (SEQ ID NO: 10)
rUrUrUrGrGrCrArArUrGrGrUrArGrArArCrUrCrArCrArCrU 11. miR-182-5p-probe-C30
                                              (SEQ ID NO: 11)
AGT GTG AGT TCT ACC ATT GCC AAA CCC CCC CCC CCC

CCC CCC CCC CCC CCC CCC 12. miR-182-5p-probe-C30-alkyne2
                                              (SEQ ID NO: 12)
AGT GTG AGT TCT ACC ATT GCC AAA CC/i5OctdU/C CCC

CCC CCC CCC CCC CCC CCC CCC
```

For single miRNA/probe hybridization, 500 µM miRNA and 500 µM of it DNA probe were mixed and melted under 95° C. for 10 min, and then gradually cooled down to the room temperature. For multiple miRNA/probe hybridization, all participating miRNAs and their probes (without and with various PEG tags) were mixed, all with the concentration of 250 µM, under 95° C. for 10 min. The mixtures were then gradually cooled down to room temperature for nanopore experiments.

Equipment:

The following instruments were used for click chemistry:
1. Controlled environment series 25 incubator shaker (New Brunswick Scientific Co., INC., Edison, N.J.)
2. Centrifuge 5415C (Eppendorf, Hauppauge, N.Y.)
3. Maxi Mix I Type 16700 Mixer (Thermolyne)

Labeling DNA Probes with Barcode Tags:

The DNA probes were labeled with PEG tags through click chemistry. The click chemistry reaction is shown in the following scheme. Specific protocol includes:

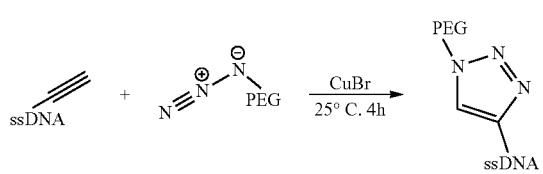

1. Mix 1 mL t-BuOH and 3 mL DMSO and vortex the mixture to obtain 3:1 DMSO/t-BuOH solvent.
2. Dissolve 1 mg CuBr in 70 μl 3:1 DMSO/t-BuOH solvent to obtain a 0.1 M solution. This solution must be freshly prepared and cannot be stored.
3. Dissolve 54 mg TBTA in 1 mL 3:1 DMSO/t-BuOH in a 0.1 M solution and store the solution at −20° C.
4. Quickly add 10 μl of the 0.1 M CuBr solution to 20 μl of the 0.1 M TBTA solution to obtain click solution.
5. Click solution (0.1 M CuBr/0.1 M TBTA 1:2 in DMSO/t-BuOH 3:1) freshly prepared prior to use.
6. Dissolve alkyne modified single-stranded DNA probe in Millipore water to obtain 2 mM DNA solution.
7. Dissolve azide modified PEG in 3:1 DMSO/t-BuOH solvent to obtain 50 mM PEG solution.
8. Dissolve 0.2461 g NaOAc in 10 mL Millipore water to obtain 0.3 M NaOAc solution.
9. Mix 10 μl of DNA solution (2 mM, 20 nmol) and 2 μl of PEG solution (50 mM, 50 nmol, and subsequently add 3 μl of a freshly prepared click solution to the mixture. The mixture is thoroughly mixed and shaken at 250 rpm in room temperature (25° C.) for 4 hours.
10. The reaction mixture is diluted with 0.3 M NaOAc (120 μl) and the DNA is precipitated using 1.5 ml cold EtOH.
11. Centrifuge the mixture at 12,000 rpm for 10 min, then remove the supernatant, and wash the precipitation twice with 1 ml cold EtOH and centrifuge the mixture at 12,000 rpm for 10 min.
12. The precipitation (purified labeled DNA) is re-dissolved in 18 μl nuclease free water, and can be used without further purification.

Single-Channel Recordings:

A membrane of 1,2-diphytanoyl-sn-glycero-3-phosphocholine is formed on a small orifice in a Teflon partition that separates two identical Teflon chambers. Each chamber contains 2 mL of electrolyte solution (1M KCl, 10 mM Tris, pH 7.4). Less than 1 ug of -haemolysin is added to one chamber with stirring, herein called the cis chamber, after a conductance increase heralds the formation of a single channel and then we start using this single channel for miRNA detection. The miRNA and its probe hybridized samples (i.e. hybridized probe/target nucleic acid complexes) were added to the cis side for ionic currents recording. Ionic currents passing through the α-hemolysin channels were measured by an AxoPatch 200B amplifier (Molecular Devices, Foster City, Calif.). Data were amplified, digitized with a DigiData 1440A (Molecular Devices), and stored on a computer using a pClamp 10.0 program (Molecular Devices). Data analysis was performed using pClamp suite software.

2. Results

Figure 2:
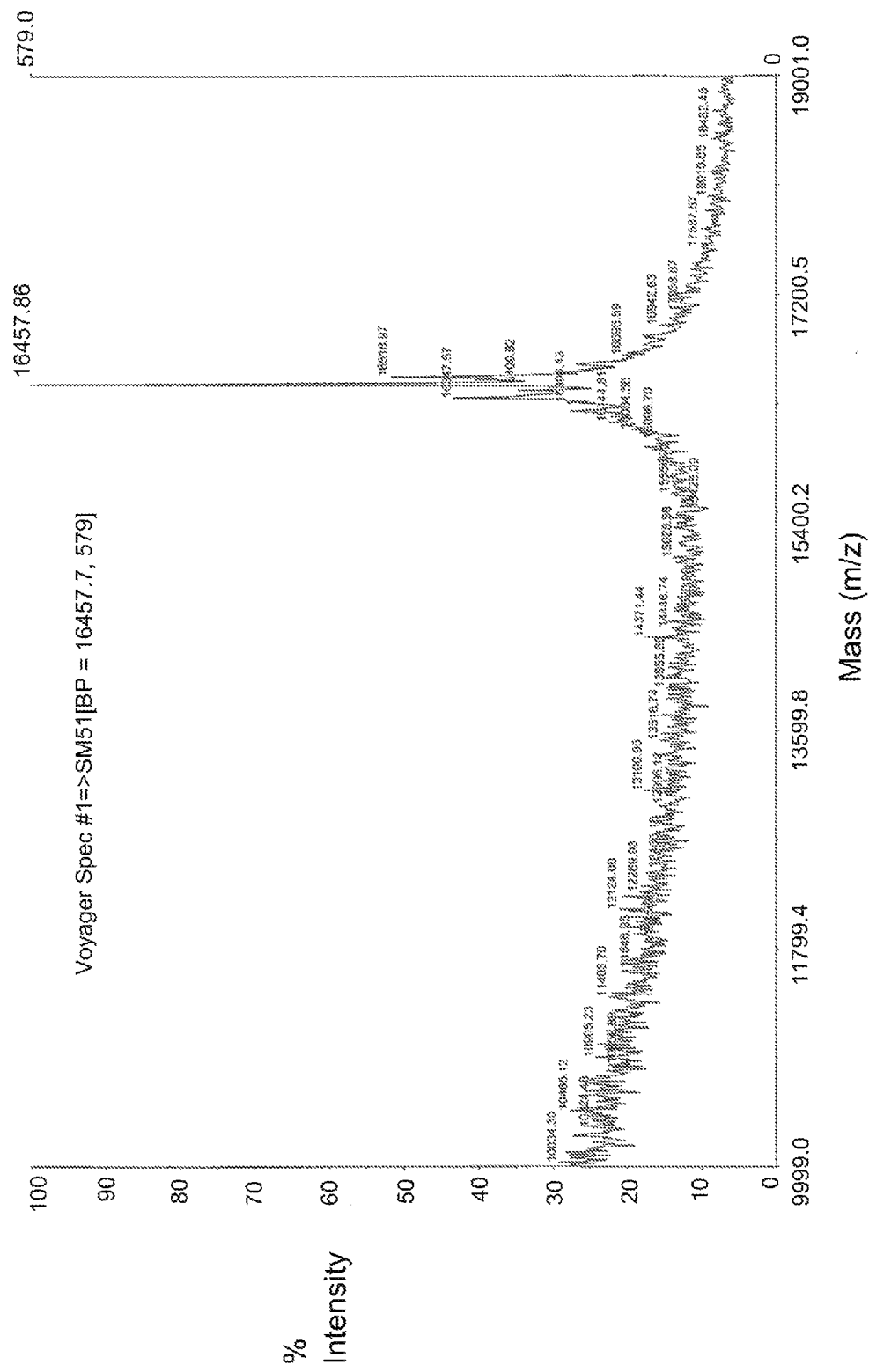
FIG. 2 shows MALDI-TOF-MS spectroscopy result for conjugation of PEG8 with the probe miR-155-probe-C30-alkyne2 through click chemistry.

Labeling DNA Probes with PEG Tags:

The probe in the nanopore sensor consists of two domains, the capture domain for hybridization with the target miRNA, and a poly(dC)$_{30}$ overhang attached to the 3' terminal, which serves to enhance the capture rate and form signatures for the miRNA•probe complex. When trapped in the nanopore, the poly(dC)$_{30}$ overhang threads the n-barrel of the pore (5 nm long). The conductance change is very sensitive to ssDNA in this region. Previous study shows that single bases of a ssDNA in this region can be discriminated[36, 37]. For an extended ssDNA, the distance between adjacent nucleotide is 0.6-0.7 nm[38]. This means, only the initial 8-9 cytosines next to the capture domain occupy the β-barrel. The labeling site is preferably within these initial 8-9 cytosines. This site is preferably not be too close to the capture domain, such as the $1^{st}$ cytosine, because it may influence the miRNA•probe hybridization. On the other hand, labeling near the pore entrance, such as the $6^{th}$ cytosine, is less sensitive and may be difficult for generating distinct signatures. The $3^{rd}$ cytosine was therefore deemed as the preferred labeling site. In this study, the probe was labeled with different sized PEG to alter the signatures to distinct conductance levels. Click chemistry was used to conjugate the PEG with the DNA probe. Click chemistry is simple and rapid; the click chemistry-enabling PEGs are commercially available (see Materials and Methods). The labeling procedure is described in Materials and Methods. The mass spectroscopy (MALDI-TOF-MS) result in FIG. 2 shows the high yield and high purity of the PEG-labeled DNA product (exemplified by miR-155-prob-C30-alkyne2-PEG8). The peak at 16457.86 Da was the product miR-155-prob-C30-alkyne2-PEG8. This peak was compared with two other peaks as shown in Table 1.

TABLE 1

| Expected [M-H] (Da) | Observed [M-H] (Da) | Difference (Da) | Relative Mass Error |
|---|---|---|---|
| 16458.91 (miR-155-probe-C30-alkyne2-PEG8) | 16457.86 (main peak) | −1.0 | −0.006% |
| | 16519.0 | −60.1 | 0.4% |
| | 16347.6 | −111.3 | 0.7% |

Figure 3:
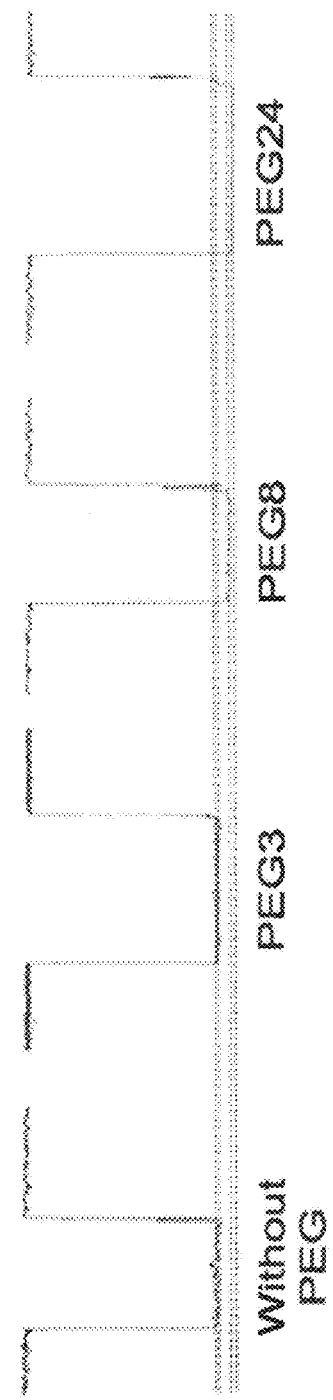
FIG. 3 shows signature current blocks for miR-155 hybridized with four probes carrying different barcode tag. The barcode design generated four distinguishable current block levels, allowing accurate assignment of each block to a specific type of probe. Currents were recorded at +120 mV in 1 M KCl buffered with 10 mM Tris (pH 7.5).

PEG Size-Dependent Signature Conductance:

First only one miRNA was utilized as the target to examine how PEG-tagged miRNA probes change the nanopore current block, in order to separate them for multiplex detection. The target miRNA was miR-155 (see Materials and Method section). The miR-155 probes were labeled with different lengths PEGS, including PEG3, PEG8, PEG24. These probes were compared with probes without labeling. FIG. 3 shows the representative signature blocks for the four miRNA•probe complexes. The residual current of signature block consistently decreased as the length of PEG extended. Using the probe without PEG labeling, the signature reduced the conductance to 12% relative to the opening pore conductance. The relative block level ($I_b/I_0$) decreased to 7.6% for PEG3 probe, 6.0% for PEG8 probe and 1.9% for PEG24 probe. These data indicate that the probe labeled with different length PEGs can alter the signature residual current.

This mechanism for regulating the signature conductance by PEG length appears universal to the detection of other miRNAs. Three miRNAs; miR-21; miR-210' and miR-182-5p, were further tested. They are all lung cancer-derived miRNA biomarkers according to the literature[4, 5]. For each miRNA, four probes were designed. They shared identical capture domain to hybridize its target. One probe was not labeled, and the other three were labeled with PEG3, PEG8 and PEG24 respectively. The mixture of each miRNA and its probe was added to the nanopore sensor. The signature current level ($I_b$) and relative block level ($I_b/I_0$) for each miRNA•probe hybrid were determined and compared in Table 2. We found that the three miRNAs, miR-21, miR-210 and miR-182-5p, revealed exactly the same trend as miR-155: i.e., the signature conductance consistently decreased as the length of PEG extended.

The results for all the four miRNAs indicate a common mechanism: the nanopore conductance is very sensitive to the PEG tag occupying the pore lumen. Without being bound by theory, it is thought that as PEG become longer, its volume expands, which blocks more space in the pore's ion pathway. As a result, the signature conductance is reduced by increasing the PEG length on the probe.

Multiplex miRNA Detection with Barcoded Probes:

Comparing probes that are identically labeled (each $I_b/I$ row in Table 2) indicates that their miRNA•probe signatures share similar conductance ($I_b/I$ in each PEG raw), and cannot discriminate miRNAs. However, for every tested miRNA ($I_b/I$ in each miRNA column), differently labeled probes produce distinct block levels in their signatures, thus the label type can be accurately discriminated.

Figure 5:
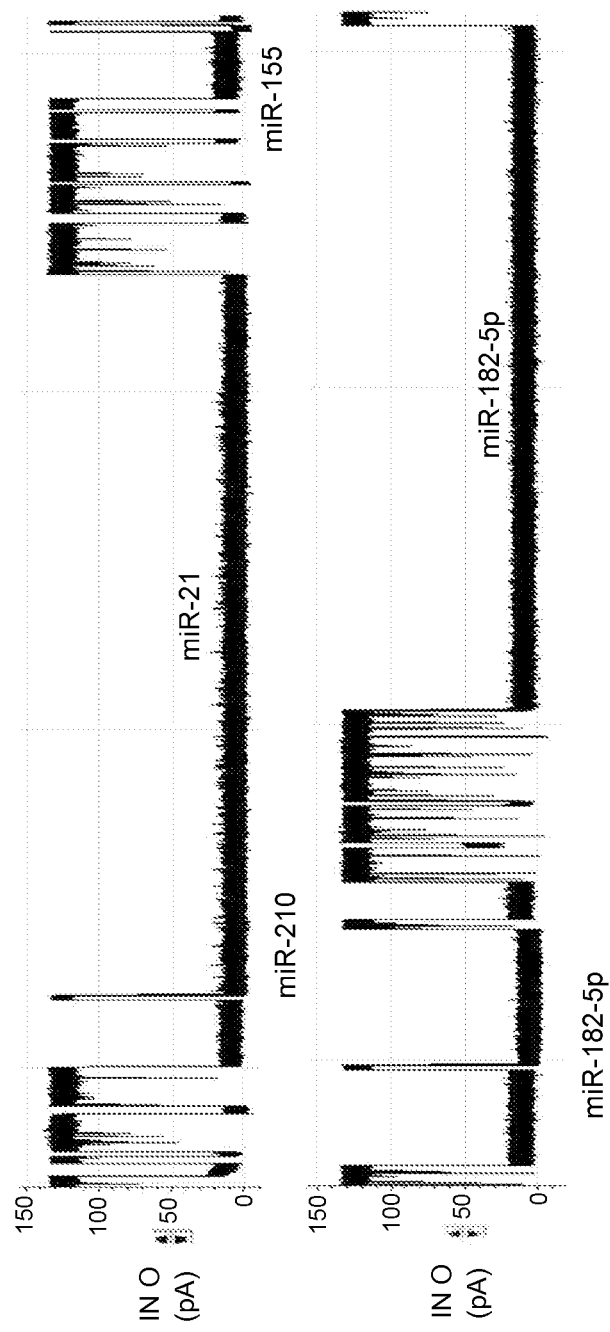
FIG. 5 shows a current trace showing simultaneous detection of multiplex miRNAs in one nanopore. Four miRNAs are presented in the solutions. miR-155 was detected by a probe without modification, miR-182-5p by a PEG3-tagged probe, miR-210 by a PEG8-tagged probe and miR-21 by a PEG24-tagged probe. Sequentially occurring signature blocks featured different current levels, representing different miRNA bound with its probe.
Figure 6:
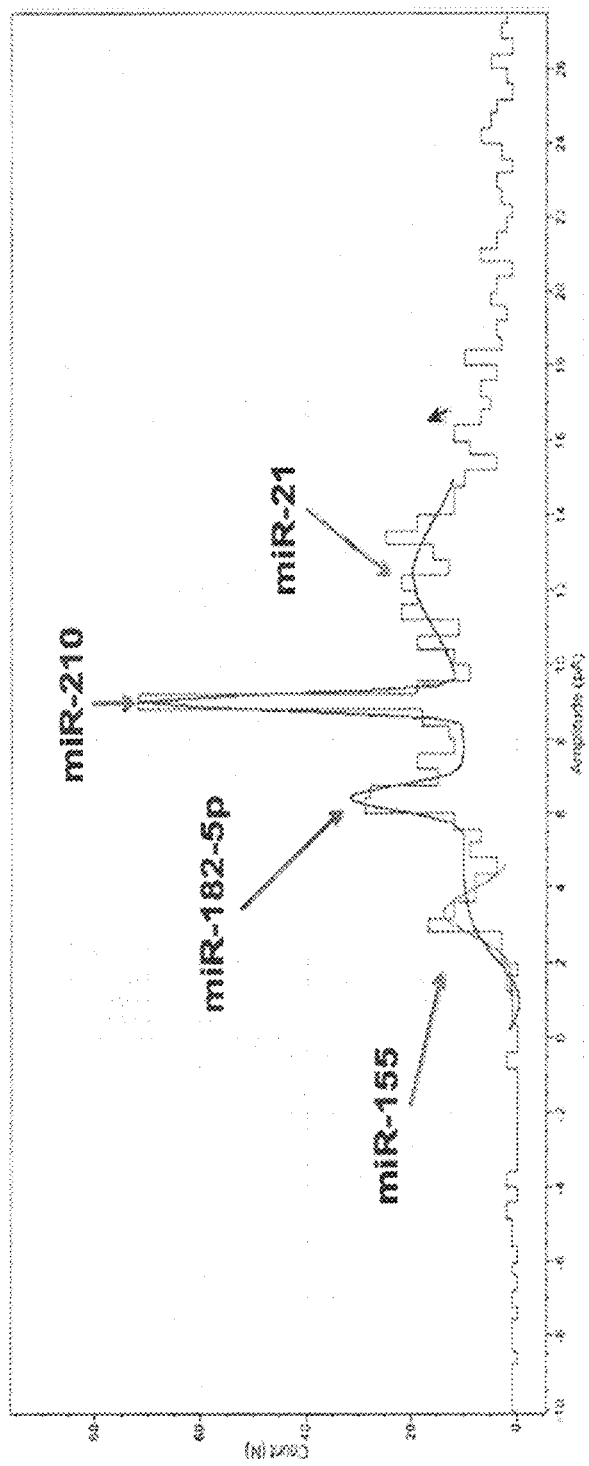
FIG. 6 shows a current amplitude histogram for counted signature blocks in multiplex miRNA detection. Four miRNAs are presented in the solutions. miR-155 was detected by a probe without modification, miR-182-5p by a PEG3-tagged probe, miR-210 by a PEGS-tagged probe and miR-21 by a PEG24-tagged probe. The four separated amplitude peaks are assigned to the four miRNAs co-existing in the mixture. The area covered each peak counts the total block number for that miRNA, which is linearly correlated to the miRNA concentration.

210 and miR-21 were mixed with their differently labeled probes. The multiplex miRNA hybridization mixture was prepared as described in the Materials and Method section. The mixture was added to the cis side of α-hemolysin pore. FIG. 5 shows the current traces for the mixture at +120 mV. The four signature conductance levels can be clearly identified, each corresponds to an miRNA. Spike-like short blocks (<1 ms) were also identified, which are caused by free miRNAs or DNA probes that rapidly translocate through the pore. The current amplitude histogram for signature events clearly demonstrates four peaks, each of which corresponds to an miRNA species. From high to low conductance, they match well with the blocking level of miR-155, miR-182-5p, miR-210 and miR-21 with their specifically labeled probes. Thus they can be attributed to miR-155, miR-182-5p, miR-210 and miR-21 respectively. The histogram has been constructed by counting the signature numbers, thus the area under each peak in the histogram can help to evaluate the concentration of each miRNA.

TABLE 2

Currents for empty nanopores (I) versus signature blocks by various miRNA•probe complexes ($I_b$) and their ratios ($I_b/I$) at +120 mV

| Tag on the probe | | miR-155 | miR-21 | miR-210 | miR-182-5p |
|---|---|---|---|---|---|
| None | I (pA) | 121.02 ± 0.03 | 117.08 ± 1.04 | 119.65 ± 0.34 | 121.49 ± 0.03 |
|  | $I_b$ (pA) | 14.56 ± 0.11 | 11.71 ± 1.07 | 12.60 ± 0.05 | 13.94 ± 0.04 |
|  | $I_b/I$ | (12.0 ± 0.1)% | (10.0 ± 1.8)% | (10.5 ± 0.3)% | (11.5 ± 0.1)% |
| PEG3 | I (pA) | 121.99 ± 0.03 | 120.10 ± 0.35 | 124.76 ± 0.23 | 125.46 ± 0.28 |
|  | $I_b$ (pA) | 9.23 ± 0.03 | 8.28 ± 0.46 | 9.51 ± 0.04 | 11.43 ± 0.03 |
|  | $I_b/I$ | (7.6 ± 0.1)% | (6.9 ± 0.7)% | (7.6 ± 0.2)% | (9.1 ± 0.3)% |
| PEG8 | I (pA) | 126.86 ± 0.32 | 122.99 ± 0.22 | 131.12 ± 0.49 | 122.59 ± 0.30 |
|  | $I_b$ (pA) | 7.60 ± 0.03 | 7.46 ± 1.35 | 7.27 ± 0.03 | 8.26 ± 0.03 |
|  | $I_b/I$ | (6.0 ± 0.3)% | (6.1 ± 1.3)% | (5.6 ± 0.4)% | (6.7 ± 0.3)% |
| PEG24 | I (pA) | 122.63 ± 0.03 | 130.16 ± 0.08 | 124.70 ± 0.33 | 118.18 ± 0.40 |
|  | $I_b$ (pA) | 2.34 ± 0.04 | 1.92 ± 0.15 | 2.51 ± 0.03 | 2.89 ± 0.03 |
|  | $I_b/I$ | (1.9 ± 0.1)% | (1.5 ± 0.2)% | (2.0 ± 0.3)% | (2.4 ± 0.4)% |

The nanopore was formed by the wild-type α-hemolysin. Four miRNAs, including miR-155, miR-21, miR-210 and miR-182-5p, were selected as the targets. Four probes were designed for each miRNA. Among them, one probe was not modified, and each of the other three was conjugated with a distinct tag as the barcode. Each miRNA was hybridized with each probe to characterize the current level of their signature blocks. Bolded values were for miRNA•probe hybrids that were selected for multiplex detection experiments (see FIGS. 4 and 5).

Figure 4:
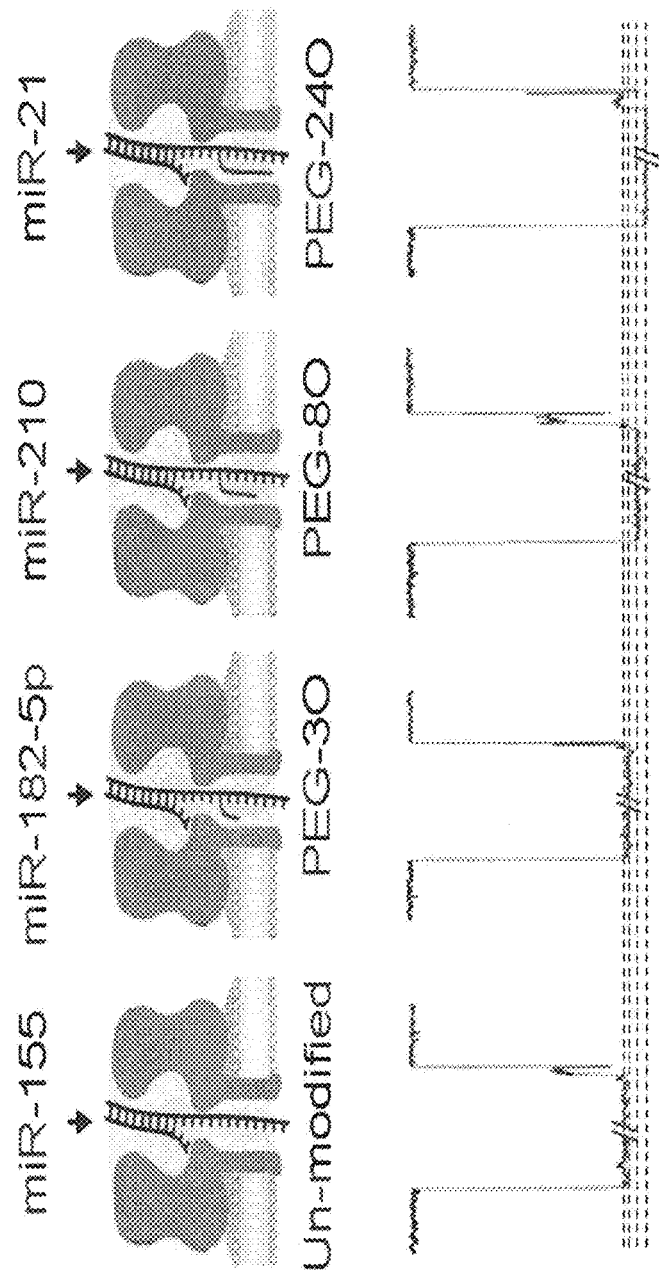
FIG. 4 shows signature current blocks generated by four miRNAs hybridized with four differently-encoded probes. Specifically, miR-155 was detected with a probe without modification, miR-182-5p by a PEG3-tagged probe, miR-210 by a PEG8-tagged probe and miR-21 by a PEG24-tagged probe. The barcode design generated four types of signatures with distinguishable current block levels. Each type of signatures corresponds to one miRNA species encoded by the probe. Currents were recorded at +120 mV in 1 M KCl buffered with 10 mM Tris (pH 7.5).

It is believed that if the probes for the four miRNAs are differently labeled, it is possible to generate distinguishable signatures to discriminate between all the miRNAs. To make the signature conductance for the four miRNAs sufficiently separate each other for accurate discrimination, the unlabeled probe with the highest residue current to target miR-155 ($I_b/I$=12%), and the PEG24-labeled probe with the lowest residue current for miR-21 ($I_b/I$=1.5%) was chosen. For the intermediate two levels, PEG3-labeled probe for miR-182-5p ($I_b/I$=9.1%) and PEGS-labeled probe for miR-210 ($I_b/I$=5.6%) was chosen. This label type/miRNA species combination maximizes the gap between different conductance levels, allowing accurate discrimination of different miRNAs. FIG. 4 clearly shows that, by using this label type/miRNA species combination, the signature blocking levels of different miRNA can be discriminated, which facilitates the multiplex detection. In a multiplex detection test, four miRNAs including miR-155, miR-182-5p, miR- Example 2

Exemplary Methods for Attaching Polyamine, Oligosaccharide, and Peptide Labels to Terminal Extension Regions of Probes Various polyamines can be attached to terminal extensions of probes by previously described methods of attaching polyamines to nucleic acids (*J. Med. Chem.* 2003, 46, 5478-5483).

Various peptides can be attached to terminal extensions of probes using previously described methods of attaching peptides to nucleic acids (Angew. Chem. Int. Ed. 2008, 47, 5565-5568)). Exemplary peptides that can be attached include, but are not limited to:

```
                                        (SEQ ID NO: 13)
His-His-His-His-His-His-Cys
and
                                        (SEQ ID NO:14)
Gly-Tyr-Tyr-Tyr-Cys.
```

Various oligosaccharides can be attached to terminal extensions of probes using previously described methods of attaching oligosaccharides to nucleic acids (Chem. Lett. 2013, 42, 197-1990).

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims. Provided herein are probes, probe sets, kits comprising the probes and probe sets, and methods of detecting one of more nucleic acids in a sample with a nanopore system. Such probes, probe sets, kits and methods encompassed by the instant invention can comprise any of the embodiments described and claimed herewith and/or any combination of embodiments described and claimed herewith.

REFERENCE LIST

1. Landi, M. T. et al. MicroRNA expression differentiates histology and predicts survival of lung cancer. Clin. Cancer Res 16, 430-441 (2010).
2. Iorio, M. V. & Croce, C. M. MicroRNAs in cancer: Small molecules with a huge impact. J. Clin. Oncol. 27, 5848-5856 (2009).
3. Mitchell, P. S. et al. Circulating microRNAs as stable blood-based markers for cancer detection. Proc. Natl. Acad. Sci. U.S.A 105, 10513-10518 (2008).
4. Zheng, D. et al. Plasma micrornas as novel biomarkers for early detection of lung cancer. Int. J. Clin. Exp. Pathol. 4, 575-586 (2011).
5. Boeri, M. et al. MicroRNA signatures in tissues and plasma predict development and prognosis of computed tomography detected lung cancer. Proc. Natl. Acad. Sci. U.S.A. 108, 3713-3718 (2011).
6. Wang, Y., Zheng, D., Tan, Q., Wang, M. X., & Gu, L. Q. Nanopore-based detection of circulating microRNAs in lung cancer patients. Nat. Nanotechnol. 6, 668-674 (2011).
7. Bayley, H. & Jayasinghe, L. Functional engineered channels and pores—(Review). Molecular Membrane Biology 21, 209-220 (2004).
8. Bayley, H. et al. Droplet interface bilayers. Mol. Biosyst. 4, 1191-1208 (2008).
9. Gu, L. Q. & Shim, J. W. Single molecule sensing by nanopores and nanopore devices. Analyst 135, 441-451 (2010).
10. Majd, S. et al. Applications of biological pores in nanomedicine, sensing, and nanoelectronics. Current Opinion in Biotechnology 21, 439-476 (2010).
11. Movileanu, L. Interrogating single proteins through nanopores: challenges and opportunities. Trends Biotechnol. 27, 333-341 (2009).
12. Venkatesan, B. M. & Bashir, R. Nanopore sensors for nucleic acid analysis. Nat Nanotechnol. 6, 615-624 (2011).
13. Ma, L. & Cockroft, S. L. Biological nanopores for single-molecule biophysics. Chembiochem 11, 25-34 (2010).
14. Howorka, S. & Si, Z. Nanopore analytics: Sensing of single molecules. Chemical Society Reviews 38, 2360-2384 (2009).
15. Olasagasti, F. et al. Replication of individual DNA molecules under electronic control using a protein nanopore. Nat. Nanotechnol. 5, 798-806 (2010).
16. Hall, A. R. et al. Hybrid pore formation by directed insertion of alpha-haemolysin into solid-state nanopores. Nat Nanotechnol. 5, 874-877 (2010).
17. Wendell, D. et al. Translocation of double-stranded DNA through membrane-adapted phi29 motor protein nanopores. Nat Nanotechnol. 4, 765-772 (2009).
18. Wanunu, M., Morrison, W., Rabin, Y., Grosberg, A. Y., & Meller, A. Electrostatic focusing of unlabelled DNA into nanoscale pores using a salt gradient. Nat. Nanotechnol. 5, 160-165 (2010).
19. Hornblower, B. et al. Single-molecule analysis of DNA-protein complexes using nanopores. Nat Methods 4, 315-317 (2007).
20. Kasianowicz, J. J., Brandin, E., Branton, D., & Deamer, D. W. Characterization of individual polynucleotide molecules using a membrane channel. Proc. Natl. Acad. Sci. U.S.A. 93, 13770-13773 (1996).
21. Branton, D. et al. The potential and challenges of nanopore sequencing. Nature Biotechnology 26, 1146-1153 (2008).
22. Cherf, G. M. et al. Automated forward and reverse ratcheting of DNA in a nanopore at 5-Å precision. Nat Biotechnol 30, 344-348 (2012).
23. Manrao, E. A. et al. Reading DNA at single-nucleotide resolution with a mutant MspA nanopore and phi29 DNA polymerase. Nat Biotechnol 30, 349-353 (2012).
24. Braha, O. et al. Simultaneous stochastic sensing of divalent metal ions. Nature Biotechnology 18, 1005-1007 (2000).
25. Gu, L. Q., Braha, O., Conlan, S., Cheley, S., & Bayley, H. Stochastic sensing of organic analytes by a pore-forming protein containing a molecular adapter. Nature 398, 686-690 (1999).
26. Kang, X. F., Cheley, S., Guan, X., & Bayley, H. Stochastic detection of enantiomers. J Am. Chem Soc 128, 10684-10685 (2006).
27. Gao, C., Ding, S., Tan, Q., & Gu, L. Q. Method of creating a nanopore-terminated probe for single-molecule enantiomer discrimination. Anal. Chem 81, 80-86 (2009).
28. Astier, Y., Braha, O., & Bayley, H. Toward single molecule DNA sequencing: direct identification of ribonucleoside and deoxyribonucleoside 5'-monophosphates by using an engineered protein nanopore equipped with a molecular adapter. J Am. Chem Soc 128, 1705-1710 (2006).
29. Clarke, J. et al. Continuous base identification for single-molecule nanopore DNA sequencing. Nat. Nanotechnol. 4, 265-270 (2009).
30. Kasianowicz, J. J., Hemickson, S. E., Weetall, H. H., & Robertson, B. Simultaneous multianalyte detection with a nanometer-scale pore. Anal. Chem. 73, 2268-2272 (2001).
31. Mitchell, N. & Howorka, S. Chemical tags facilitate the sensing of individual DNA strands with nanopores. Angew. Chem. Int. Ed Engl. 47, 5565-5568 (2008).
32. Borsenberger, V., Mitchell, N., & Howorka, S. Chemically labeled nucleotides and oligonucleotides encode DNA for sensing with nanopores. J. Am. Chem. Soc. 131, 7530-7531 (2009).
33. Robertson, J. W. et al. Single-molecule mass spectrometry in solution using a solitary nanopore. Proc Natl. Acad. Sci. U.S. A 104, 8207-8211 (2007).
34. Kumar, S. et al. PEG-labeled nucleotides and nanopore detection for single molecule DNA sequencing by synthesis. Sci. Rep. 2, 684 (2012).
35. An, N., Fleming, A. M., White, H. S., & Burrows, C. J. Crown ether-electrolyte interactions permit nanopore detection of individual DNA abasic sites in single molecules. Proc. Natl. Acad. Sci. U.S. A 109, 11504-11509 (2012).
36. Purnell, R. F., Mehta, K. K., & Schmidt, J. J. Nucleotide identification and orientation discrimination of DNA homopolymers immobilized in a protein nanopore. Nano Lett 8, 3029-3034 (2008).
37. Stoddart, D., Heron, A. J., Mikhailova, E., Maglia, G., & Bayley, H. Single-nucleotide discrimination in immobilized DNA oligonucleotides with a biological nanopore. Proc Natl Acad Sci USA 106, 7702-7707 (2009).
38. Murphy, M. C., Rasnik, I., Cheng, W., Lohman, T. M., & Ha, T. Probing single-stranded DNA conformational flexibility using fluorescence spectroscopy. Biophys. J. 86, 2530-2537 (2004).
39. Na, A., Fleming, A. M., White, H. S. & Burrows, C. J. Crown Ether-Electrolyte Interactions Permit Nanopore Detection of Individual DNA Abasic Sites in Single Molecules. *Proceedings of the National Academy of Sciences,* 1-6, doi:10.1073/pnas.1201669109/-/DCSupplemental (2012).

---

What is claimed is:

1. A set of probe molecules comprising at least a first probe molecule and a second probe molecule each comprising:
   a) a capture domain that comprises a sequence with complementarity to a target nucleic acid;
   b) a terminal extension that is covalently linked to the 5' end, the 3' end, or both the 5' end and the 3' end of the capture domain; and
   c) at least one polymer label branched from an internal residue located within at least one of the terminal extension(s), wherein the nucleic acid capture domain of the first probe molecule comprises a sequence with complementarity to first target nucleic acid and the nucleic acid capture domain of the second probe molecule comprises a sequence with complementarity to a second target nucleic acid, wherein the polymer label is a polyglycol selected from the group consisting of polyethylene glycol (PEG), methoxypolyethylene glycol (MPEG), polypropylene glycol (PPG), polybutylene glycols (PBG), and copolymers thereof wherein the polymer label of the first probe molecule is different from the polymer label of the second probe molecule, and wherein the polymer labels of the first and second probe molecules provide for independent detection of the first and second target nucleic acids in a nanopore system.

2. The probe set of claim 1, wherein the polymer labels of the first and second probe molecules provide for distinct signature conductance blocks when hybridized with their respective targets and subjected to an applied voltage in a nanopore system.

3. The probe set of claim 1, wherein the polymer label of at least one of the first probe molecule or the second probe molecule is a hydrophilic homopolymer or a hydrophilic heteropolymer.

4. The probe set of claim 1, wherein the capture domain and terminal extension of at least one of the first probe molecule or the second probe molecule are independently selected from the group consisting of nucleic acids and peptide nucleic acids.

5. The probe set of claim 1, wherein the terminal extension of at least one of the first probe molecule or the second probe molecule is covalently linked to the 3' terminus of the capture domain.

6. The probe set of claim 1, wherein the terminal extension of at least one of the first probe molecule or the second probe molecule is selected from the group consisting of poly(dC)$_{(27-33)}$, poly(dG)$_{(27-33)}$, poly(dA)$_{(27-33)}$, poly(dT)$_{(27-33)}$, and poly(dN)$_{(27-33)}$, where N is any combination of cytosine, guanosine, adenosine, thymine, an abase, inosine, xanthosine, 7-methylguanosine, dihydrouridine, and 5-methylcytidine.

7. The probe set of claim 1, wherein the probe set comprises at least one additional probe molecule that comprises:
   a) a capture domain that comprises a sequence with complementarity to a target nucleic acid;
   b) a terminal extension that is covalently linked to the 5' or 3' end of the capture domain; and
   c) at least one polymer label branched from an internal residue located within at least one of the terminal extension(s),
   wherein the nucleic acid capture domain of the additional probe molecule(s) comprises a sequence with complementarity to a target nucleic acid that is distinct from the first and second target nucleic acids and wherein the polymer label of each additional probe molecule(s) is different from the polymer label of the first probe molecule, second probe molecule, and any other additional probe molecules and provides for independent detection of the first target, second target, and additional target nucleic acids in a nanopore system.

8. The probe set of claim 1, wherein the polymer label attached to the terminal extension of the first probe molecule is a polyethylene glycol having a length and the label attached to the extension of the second probe molecule is a polyethylene glycol of a different length than the length of the polyethylene glycol attached to the first probe molecule.

9. The probe set of claim 1, further comprising a probe with a capture domain comprising a sequence with complementarity to an additional distinct target nucleic acid and, optionally, a terminal domain, wherein said probe lacks a polymer label and provides for independent detection of the additional distinct target nucleic acid.

10. The probe set of claim 1 wherein the polymer label of at least one of the first probe molecule or the second probe molecule is branched from an internal residue of the terminal extension that is located within nine residues of 5' or 3' covalent linkage of the terminal extension to the capture domain.

11. The probe set of claim 10, wherein the polymer label is branched from the second to the fifth internal residue of the terminal extension that is located 5' or 3' from the covalent linkage to the capture domain.

12. A method for detecting at least two distinct single stranded target nucleic acids in a sample with a nanopore system, the method comprising:
  a) contacting the sample with a set of at least two probe molecules and allowing the probe molecules to hybridize with a target nucleic acid present in the sample to form a hybridized sample, wherein the set of probe molecules comprises at least a first probe molecule and a second probe molecule, both of which comprise:
    (i) a capture domain that comprises a sequence with complementarity to a target nucleic acid;
    (ii) a terminal extension that is covalently linked to the 5' end 3' end, or both the 5' end and the 3' end of the capture domain; and
    (ii) at least one polymer label branched from an internal residue located within at least one of the terminal extension(s),
  wherein the nucleic acid capture domain of the first probe molecule hybridizes with a first target nucleic acid and the nucleic acid capture domain of the second probe molecule hybridizes with a second target nucleic acid, and wherein the polymer label of the first probe molecule is different from the polymer label of the second probe molecule;
  b) applying a voltage to said hybridized sample mixture in a cis compartment of a dual chamber nanopore system sufficient to trap a hybridized probe/target nucleic acid complex in the nanopore and drive translocation of said hybridized probes and target nucleic acids through a nanopore of said system by an unzipping process, and,
  c) analyzing an electrical current pattern in said nanopore system over time, wherein a presence of said distinct single stranded target nucleic acids in the sample is indicated by occurrence of two distinct signature electrical current blocks corresponding to trapping of each distinct hybridized probe and target nucleic acids in the nanopore.

13. The method of claim 12 wherein the presence a first target nucleic acid and the presence of a second target nucleic acid in the sample result in distinct signature electrical current blocks that are distinct signature conductance blocks.

14. The method of claim 12, wherein the label attached to the terminal extension of the first probe molecule is a polyethylene glycol having a length and the label attached to the extension of the second probe molecule is a polyethylene glycol of a different length than the polyethylene glycol attached to the first probe molecule.

15. The method of claim 12, wherein the polymer label of at least one of the first probe molecule or the second probe molecule is branched from an internal residue of the terminal extension that is located within nine residues of 5' or 3' covalent linkage of the terminal extension to the capture domain.

16. The method of claim 15, wherein the polymer label is branched from the second to the fifth internal residue of the terminal extension that is located 5' or 3' from the covalent linkage to the capture domain.

17. A method for detecting at least one distinct single stranded target nucleic acid in a sample with a nanopore system, the method comprising:
  a) contacting the sample with a set of probe molecules comprising a probe molecule that comprises: (i) a capture domain that comprises a sequence with complementarity to a target nucleic acid; (ii) a terminal extension that is covalently linked to the 5' end, the 3' end, or both the 5' and 3' end of the capture domain, and (iii) at least one polymer label branched from an internal residue located within at least one terminal extension, wherein said probe molecule provides for detection of the target nucleic acid in a nanopore system and allowing the probe molecule to hybridize with a target nucleic acid present in the sample to form a hybridized sample, wherein the probe molecule is a first probe molecule and the set of probe molecules further comprises a second probe molecule;
  b) applying a voltage to said hybridized sample mixture in a cis compartment of a dual chamber nanopore system sufficient to trap a hybridized probe/target nucleic acid complex in the nanopore and drive translocation of said hybridized probe and target nucleic acid through a nanopore of said system by an unzipping process, and,
  c) analyzing an electrical current pattern in said nanopore system over time, wherein a presence of said distinct single stranded target nucleic acid in the sample is indicated by occurrence of a distinct signature electrical current block corresponding to translocation of the hybridized probe and target nucleic acid through the nanopore.

* * * * *